United States Patent [19]

Thomas, Jr.

[11] 4,168,623
[45] Sep. 25, 1979

[54] METHOD FOR DETERMINING VOLATILE CONTENT OF A SAMPLE

[75] Inventor: Charles E. Thomas, Jr., Richmond, Va.

[73] Assignee: Philip Morris Incorporated, New York, N.Y.

[21] Appl. No.: 766,358

[22] Filed: Feb. 7, 1977

[51] Int. Cl.² .................. G01N 5/04; G06F 15/46
[52] U.S. Cl. ....................... 73/76; 73/15 R; 177/25; 364/497; 364/526; 364/567
[58] Field of Search ............... 73/76, 15 R; 131/22 R, 131/22 A, 21 A; 177/1, 25; 58/153; 364/497, 526, 567

[56] References Cited

U.S. PATENT DOCUMENTS

| 2,539,754 | 1/1951 | Rettinger et al. ............... 58/153 X |
| 3,091,301 | 5/1963 | Stone ............................... 177/1 |
| 3,795,099 | 3/1974 | Tsuruishi ........................ 58/153 X |
| 3,840,025 | 10/1974 | Fowler et al. ................. 131/21 A X |
| 3,875,395 | 4/1975 | Olomouc ........................... 364/497 |
| 3,909,598 | 9/1975 | Collins et al. .................. 177/25 X |
| 3,916,670 | 11/1975 | Davis et al. ...................... 73/76 X |
| 3,973,431 | 8/1976 | Ginhous et al. .................... 73/76 |

FOREIGN PATENT DOCUMENTS 2275766 1/1976 France ................................. 73/76

Primary Examiner—Daniel M. Yasich
Attorney, Agent, or Firm—Watson, Leavenworth, Kelton & Taggart

[57] ABSTRACT

Volatile content of a sample is determined by volatilizing a portion of such content, taking weight measurements at uniform intervals during such volatilization after a preselected delay, obtaining differences between weight measurements taken at times separated by a predetermined uniform measure and processing such weight differences.

8 Claims, 9 Drawing Figures

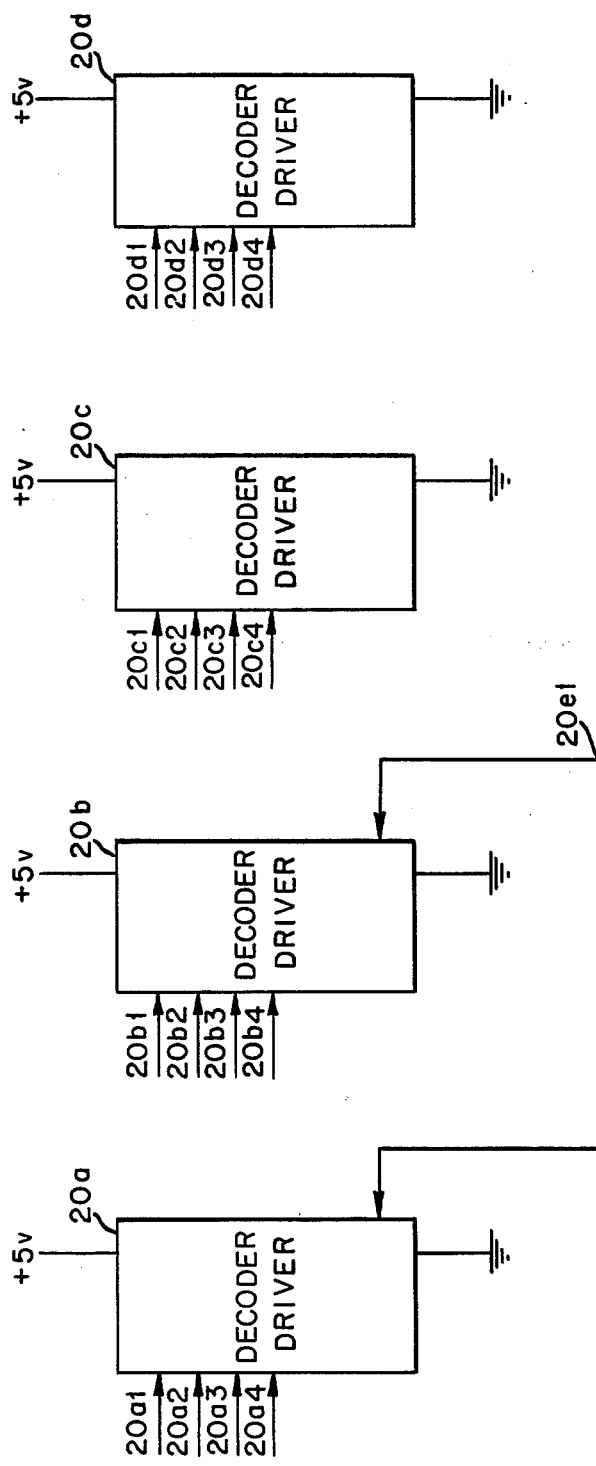
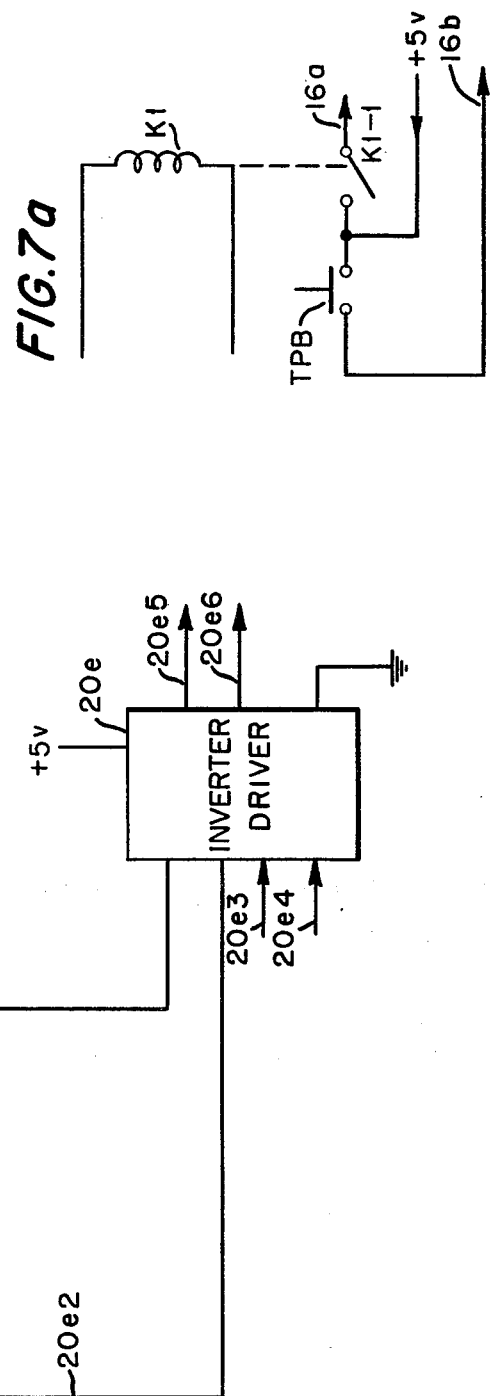
FIG.7a
FIG.7b

METHOD FOR DETERMINING VOLATILE CONTENT OF A SAMPLE

FIELD OF THE INVENTION

This invention relates generally to methods for ascertaining volatile content of samples and, more particularly, to methods for determining the water content of water-containing substances, such as tobacco.

BACKGROUND OF THE INVENTION

In a long-standing practice in the tobacco industry, tobacco samples are examined for water content by heating in an oven. In such practice, the sample is subjected to oven heating for a standardized length of time at a predetermined temperature. The water content, expressed as oven volatiles (O.V.), is calculated from the weight loss in this process.

Two evident disadvantages attend such oven volatilization practice. Firstly, an extended time period is required. Secondly, for many materials containing oven volatiles, the rate of volatilization of water exceeds the rate of volatilization of other volatiles during early heating stages, whereas the converse is true of such rates as heating progresses into final heating stages. Thus, in such extended heating practice, the observed weight loss can be substantially different from actual weight loss attributable to water volatilization. Water content calculation based on observed weight loss over extended heating accordingly may have inherent inaccuracy.

SUMMARY OF THE INVENTION

It is an object of the present invention to provide improved methods for determining volatile content of samples.

The invention has as more particular objects thereof the lessening of time requirements in oven volatilization practices and improvements in accuracy of results obtained thereby as respects selected volatiles.

In attaining the foregoing and other objects, the invention provides for obtaining information sufficient to determine sample volatile content without need for obtaining a measurement of sample weight at the end of extended heating time periods. Since the time period for heating the sample is shortened, information is derived under conditions in which volatiles other than a selected volatile may remain in the sample and not adversely affect the accuracy of weight loss measurement for use in determining the content percentage of such selected volatile.

Fundamental to the invention is applicant's realization that volatile loss attributable to sample heating is an exponential function. From this basis, applicant has determined a time schedule for the taking of weight measurements in the course of sample heating and further has established computational parameters for processing such weight measurements to yield, for example, water content information. As is noted in detail hereinafter, control of the scheduling of weight measurements and computation of water content as a percentage of sample weight is readily enabled by use of a digital computer, suitably programmed.

The foregoing and other objects and features of the invention will be evident from the following detailed description of preferred practices in accordance with the invention.

DESCRIPTION OF THE DRAWINGS

FIG. 7a is a circuit diagram of the tare weight control of FIG. 7.

FIG. 7b is a diagram of the display circuitry of FIG. 7

DESCRIPTION OF PREFERRED PRACTICES

Figure 1:
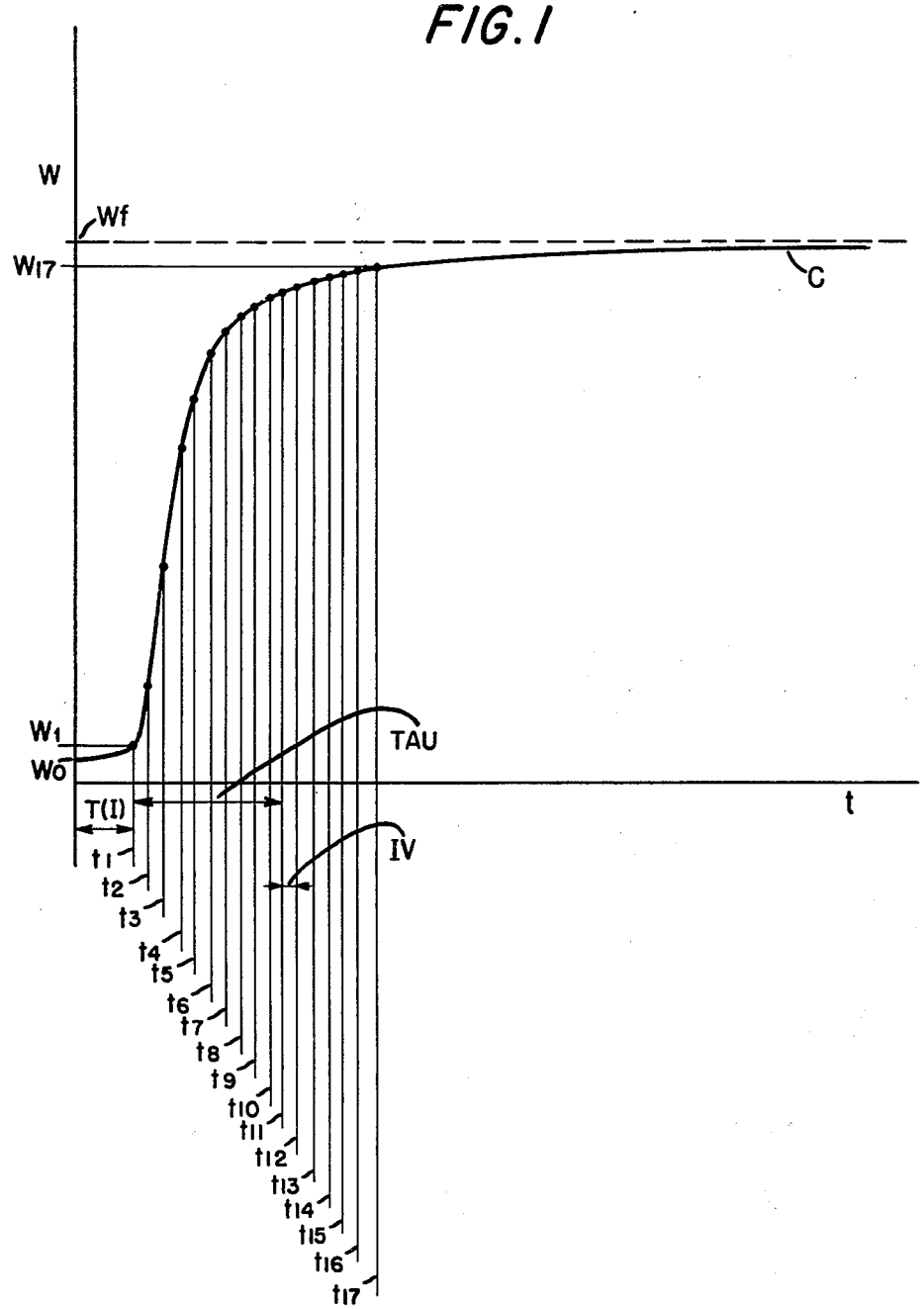
FIG. 1 is a graphical illustration helpful to an understanding of the invention.

Referring to FIG. 1, curve C depicts a weight decrease vs. time characteristic of a tobacco sample upon being heated in an oven at time $t=0$. Initial weight is identified as $W_o$. Were heating of the sample to continue for the standardized time discussed above, final weight would be $W_f$. Such curve, by applicant's determination, is exponential involving a constant (k), whose value is dependent on the intensity of applied thermal energy and may be ascertained once $W_o$ and $W_f$ are known.

Applicant's procedure for reaching knowledge of such constant without such extended heating of the sample will be seen from the following.

$$W_t = W_f + (W_o - W_f)e^{-kt} \tag{1}$$

$$\% W = \frac{W_o - W_f}{W_o} = \frac{W_o - W_t}{W_o(1 - e^{-kt})} \tag{2}$$

$$\frac{W_o - W_{t1}}{W_o - W_f} - \frac{W_o - W_{t2}}{W_o - W_f} = (1 - e^{-kt1}) - (1 - e^{-kt2}) \tag{3}$$

where $t_2 - t_1 = IV$ (FIG. 1) or more generally:

$$\frac{W_o - W_t}{W_o - W_f} = 1 - e^{-kt} \tag{4}$$

$$\frac{W_o - W_t}{W_o - W_f} - \frac{W_o - W_f}{W_o - W_f} = -e^{-kt} \tag{5}$$

$$\frac{W_t - W_f}{W_o - W_f} = e^{-kt} \tag{6}$$

$$W_t - W_f = (W_o - W_f)e^{-kt} \tag{7}$$

With $\tau$ (TAU, FIG. 1) assumed as a constant unit of time:

$$W_{(t+\tau)} - W_f = (W_o - W_f)e^{-k(t+\tau)} \tag{8}$$

subtracting (8) from (7):

$$W_t - W_{(t+\tau)} = e^{-kt}(W_o - W_f)(1 - e^{-k\tau}) \tag{9}$$

taking the natural logarithm of both sides $$\ln(W_t - W_{(t+\tau)}) = -kt + \ln(W_o - W_f) + \ln(1 - e^{-k\tau}) \tag{10}$$

This equation is that of a straight line $$Y = BX + A \tag{11}$$

With slope B and intercept A.

By taking weight values at equally spaced times after delay T(I) (FIG. 1) and by obtaining differences between those weight values spaced in time by $\tau$, one may identify a linear relationship between the natural logarithms of such weight values and such times and determine slope B by a least-squares fit program. With B and hence k now known, the percent weight loss may be determined from equation (2).

Percent weight loss may alternatively be determined by introducing the now known k into the intercept terms of equation (10). Such terms may be rewritten as follows:

$$A = \ln(W_o - W_f) + \ln(1 - e^{k\tau}) \quad (12)$$

$$e^A = (W_o - W_f)(1 - e^{k\tau}) \quad (13)$$

$$\frac{e^A}{1 - e^{k\tau}} = W_o - W_f \quad (14)$$

$$\frac{1}{W_o} \times \frac{e^A}{1 - e^{k\tau}} = \frac{W_o - W_f}{W_o} \quad (15)$$

yielding such percent weight loss as a function of initial weight, intercept, slope and time spacing between differenced weights. A particularly preferred practice of the invention averages results obtained from these two approaches, i.e., equations (2) and (15), to ascertain sample water content.

Referring now to FIGS. 2–6, a flow chart for use in practicing the method of the invention in part by digital computer identifies an analog balance as providing its output in item 100, analog-to-digital conversion in item 101 and a start button in item 102. Operation of such start button directs, by instruction 103, that the interval (IV) between weight measurements be five seconds and that the interval (TAU) between measurements which are to be differenced be set at fifty seconds. Instructions 104 and 105 provide that the digitized balance weight be taken if the tare button is on. Instructions 106 and 107 provide that time be counted in seconds commencing at the time that the oven is turned on. Instruction 108 calls for a one second delay after oven turn-on (to allow pan stabilization after vibration) at which time instruction 109 directs that the digitized balance weight be taken, the balance pan now containing the tobacco sample. Instruction 110 directs that the initial weight be computed by subtracting tare weight from the weight read under instruction 109. Instruction 111 provides for reading the time-setting of a thumbwheel.

Figure 2:
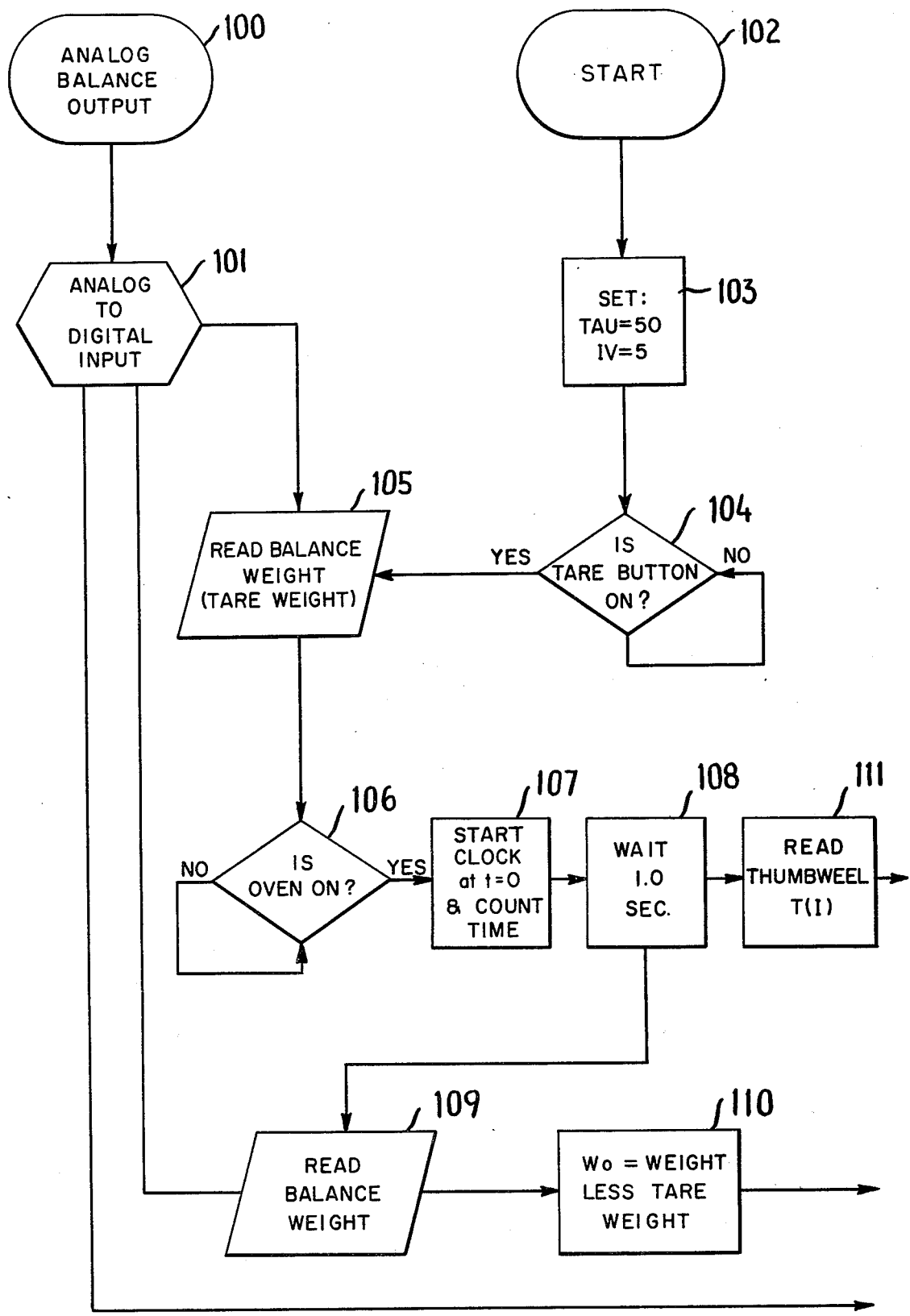
FIGS. 2–6 disclose a flow chart of a computer program for use in practicing the invention.
Figure 3:
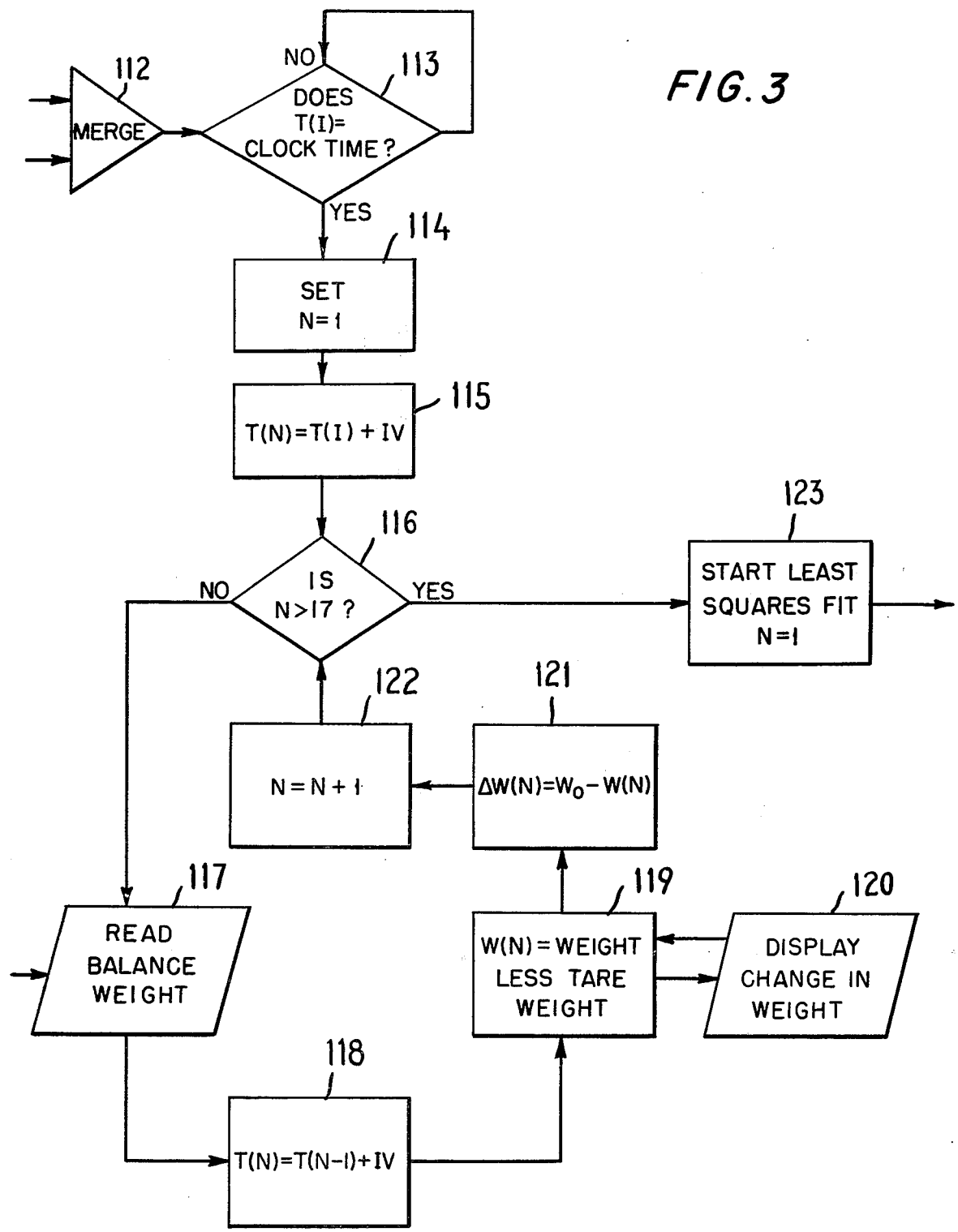

Turning to FIG. 2, instructions 112 and 113 provide indication that clock time has reached the time set by the thumbwheel with instruction 114 then setting N equal to unity and instruction 115 identifying the weight-taking time as the thumbwheel time incremented by interval IV.

Instruction 116 inquires as to whether N is greater than seventeen and, for N values not greater than seventeen, instruction 117 provides that the digitized balance weight be read. Instruction 118 establishes the next weight-taking time as being spaced from the previous taken weight by interval IV. Instruction 119 subtracts tare weight from such taken weight with instruction 120 calling for display of change in weight between successively taken weights. Instruction 121 computes the change in weight with respect to the initially taken weight. Instruction 122 increments N by one. The cycle directed by instructions 116 through 122 is repeated seventeen times, thereby providing for the taking of seventeen weights spaced uniformly by interval IV and commencing at a time equal to the thumbwheel time setting plus interval IV. Instruction 123 then directs that a least squares fit cycle commence to identify a line common to the first seven weights taken, as directed by instruction 124.

Figure 4:
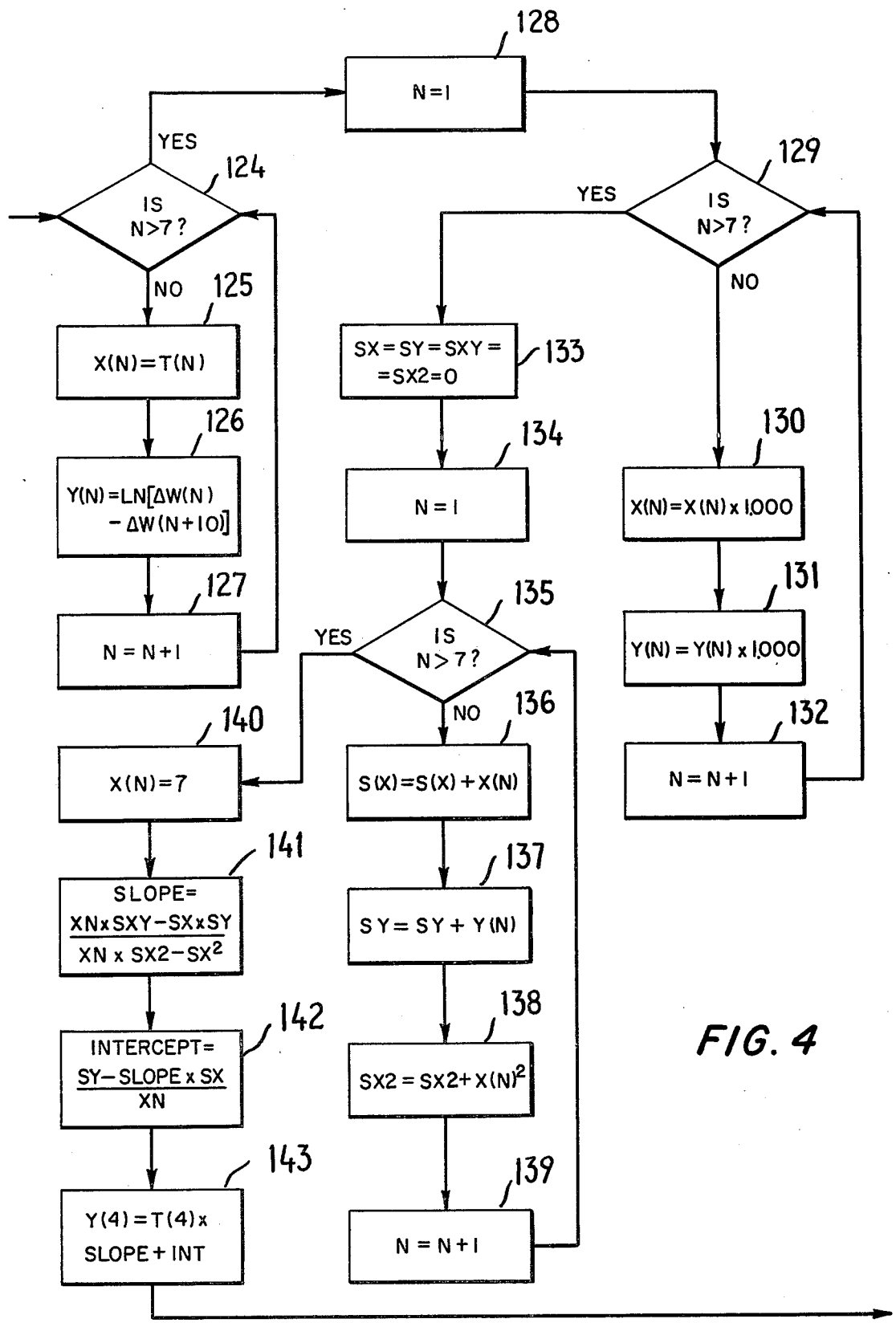

Turning to FIG. 4, instruction (125) sets X values for such line equal to the seven times involved, selected as the times of the earlier-taken of the differenced weights. Instruction (126) directs that weights spaced by 50 seconds (TAU) be differenced and that the natural logarithm of each such difference be determined and assigned as a Y value for such line. Instruction (127) increments N by one and, after N=7 X and Y values are defined, instruction 128 sets N again equal to unity. Instructions 129 through 132 direct that three decimal places be provided for the X and Y values. Instruction (129) advances after N=7 to instruction (133) which sets various parameters to zero, namely: SX, sum of the X values; SY, sum of the Y values; SXY, sum of the products of X and Y; and SX2, sum of the squares of the X values. Instruction (134) sets N again equal to unity.

For the seven pairs of logarithm values and times, instructions (135) through (139) compute SX, SY and SX2. Instruction (140) sets XN equal to 7. Instruction (141) computes the slope of the line common to the logarithm values and times and instruction (142) determines the intercept value. Computation is made by instruction (143) of Y for N equal to four, discussed below.

A program for implementing the foregoing by a general purpose computer, such as a Xerox Sigma 8 computer, is set forth below in hybridized Dartmouth basic language. Weight and time information is pre-obtained and stored for access of the computer. The invention is realized in a more adaptive microprocessor embodiment discussed hereinafter.

| | |
|---|---|
| (103A) | TAU = 50 |
| (103B) | IV = 5 |
| (105) | READ TARE WT |
| (107) | COUNT TIME FROM T=0 |
| (108) | WAIT 1 SEC |
| (109) | READ BALANCE WT |
| (110) | WO = BALANCE WT − TARE WT |
| (111) | READ THUMBWHEEL TIME = T(I) |
| (114) | AT T = T(I) SET N=0 |
| (115) | SET T(N) = T(I) + IV |
| (116) | FOR N = 1 TO 17 |
| (117) | READ BALANCE WT = W(N) |
| (118) | T(N) = T(N−1) + IV |
| (119) | W(N) = BALANCE WT − TARE WT |
| (121) | ΔW(N) = WO − W(N) |
| (122) | N = N + 1 |
| (123) | AT N > 17, SET N = 1 |
| (124) | FOR N = 1 TO 7 |
| (125) | X(N) = T(N) |
| (126) | Y(N) = LN [ΔW(N) − ΔW(N+10)] |
| (127) | N = N + 1 |
| (128) | AT N > 7, SET N = 1 |
| (129) | FOR N = 1 TO 7 |
| (130) | X(N) = X(N)*1.000 |
| (131) | Y(N) = Y(N)*1.000 |
| (132) | N = N + 1 |
| (133) | SET SX = SY = SXY = SXZ + 0 |
| (134) | AT N > 7, SET N = 1 |
| (135) | FOR N = 1 TO 7 |
| (136) | SX = SX + X(N) |
| (137) | SY = SY + Y(N) |
| (138) | SX2 = SX2 + X(N)**2 |
| (139) | N = N + 1 |
| (140) | AT N > 7, SET XN = 7 |
| (141A) | DENOM = XN* SX2 − SX**2 |
| (141B) | SLOPE = (XN* SXY − SX*SY)/DENOM |
| (142) | INT = (SY − SLOPE**SX)/XN |

-continued (143)        Y(4) = T(4)*SLOPE + INT

Preselection of a T(I) value for delaying the taking of the initial weight measurement during heating is found necessary by applicant to limit the influence of a second order effect at the start of the heating cycle, namely, that of diffusion. Such influence may be further reduced as a factor adversely affecting accuracy in water content determination by the following practice wherein weight values taken at later times in the cycle are employed to correct earlier-derived weight information. Second order effects capable of influencing such later-derived weight values, namely, substantial volatilization of matter other than water, are lessened by that aspect of this invention which provides for all needed weight measurements to be taken in the course of early heating stages.

Figure 5:
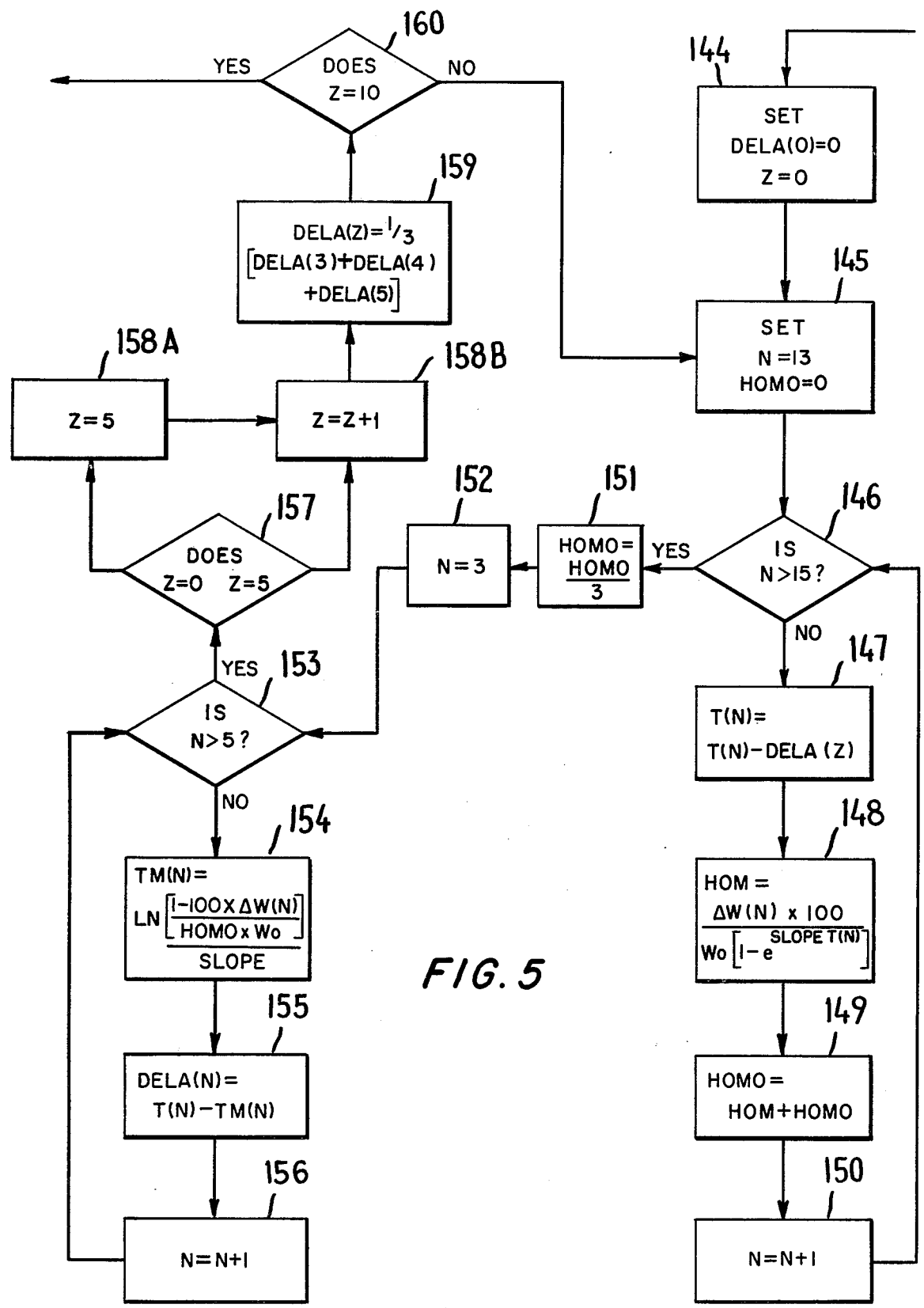

Referring to FIG. 5, flow chart instruction (144) sets parameters DELA(0) and Z equal to zero. Instruction (145) sets N equal to thirteen and a parameter HOMO equal to zero. Instructions (146) through (150) provide for computation of HOMO values for N at 13, 14 and 15 (later-taken weights) and averaging thereof is performed per instruction (151). In instruction 147, for the initial HOMO averaging practice T(N) is unchanged from its prior values since no DELA(Z) has yet been provided from instruction (159).

Instruction (148) computes, in effect:

$$HOM = \frac{\frac{W_o - W_t}{W_o}}{1 - e^{-kt}} \quad (16)$$

With HOMO so averaged for N=13, 14, 15 and DELA(Z) equal to zero, new times are computed for low N values based on the averaged HOMO, thereby to provide a DELA(Z).

For this purpose, instruction (152) sets N equal to 3. Instruction (153) directs that TM(N), modified time, and DELA(N) be computed for N equal to 3, 4 and 5. That the computation in instruction (154) yields time information may be seen from it as rewritten below:

$$TM(N) = \frac{1}{k} LN \frac{W_o - W_t}{W_o(HOMO)} \quad (17)$$

$$= \frac{1}{k} LN(1 - e^{-kt}) = t \quad (18)$$

Instruction (155) sets DELA(N) 3, 4, 5 equal to the difference between T(N), actual weight taking times, and TM(N), modified times based on HOMO 13, 14, 15. Instruction (157) inquires as to the value of Z. IF Z is five, instructions (158A) and (158B) provide for five complete iterations of instructions (145) through (159). If Z is zero, ten such iterations are completed under direction of instruction (160).

Figure 6:
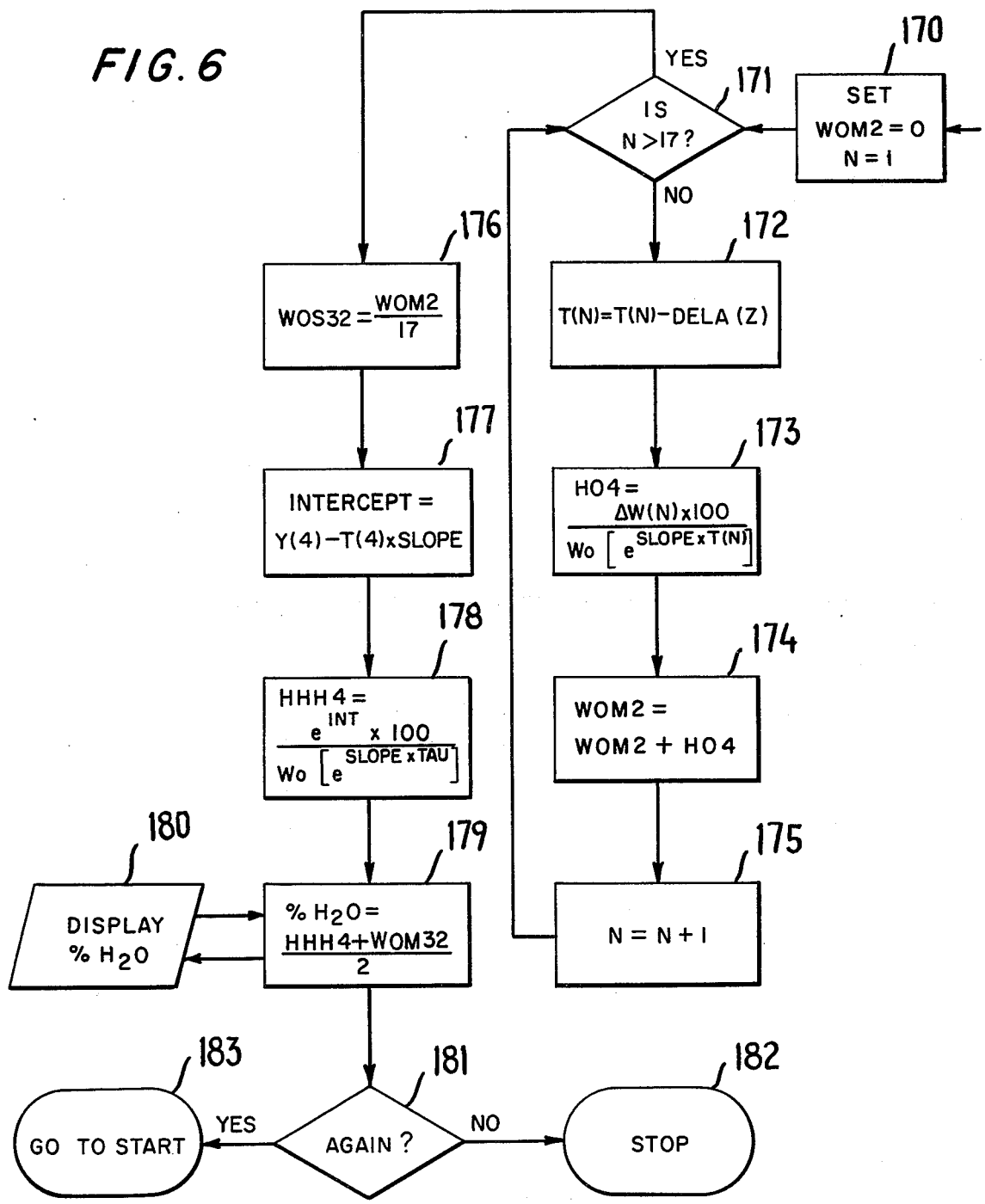

Turning now to FIG. 6, instruction (170) sets parameter WOM2 equal to zero and sets N again equal to unity. Instructions (171) through (175) provide that, for each of the seventeen weight values taken, sample water content be computed based on new times derived under instruction (172). Instruction (172) identifies such new times as differing from the actual weight-taking time by DELA(Z) as last computed. Instruction (173) directs computation of parameter HO4 (water content percent) based on measured weights, computed slope and new time. Instruction (174) accumulates such percentages as parameter WOM2.

Instruction (176) averages the accumulated percentages as parameter WOS32. Instruction (177) computes new intercept based on the new time for the fourth-taken measurement.

Instruction (178) now looks to the alternate method noted above and computes water content percent as HHH4, which will be seen to be $$HHH4 = \frac{e^A}{W_o e^{-kt}} \quad (19)$$

This computation uses intercept information from instruction (177) and TAU value.

Percent water content is now determined under instruction (179) by averaging the results of computations under instructions (176) and (178). Instruction (180) provides for display of the water content percent. Instructions (181), (182) and (183) permit stopping or repeating the entire practice.

Continuing the above program, the step listing for this practice is as follows:

| | |
|---|---|
| (144) | DELA(0) = 0 Z = 0 |
| (145) | N = 13 HOMO = 0 |
| (146) | FOR N = 13 TO 15 |
| (147) | T(N) = T(N) − DELA(Z) |
| (148A) | HON = 1 − EXP (SLOPE*T(N) |
| (148B) | HOM = ΔWT(N)/WO/HON |
| (149) | HOMO = HOMO + HON |
| (150) | N = N + 1 |
| (151) | HOMO = HOMO/3 |
| (152,153) | FOR N = 3 TO 5 |
| (154) | TM(N) = 1/SLOPE*LN((100*W(N))/(HOMO*WO) |
| (155) | DELA(N) = T(N) − TM(N) |
| (156) | N = N + 1 |
| (157) | IF Z = 0 Z = 5 |
| (158B) | Z = Z + 1 |
| (159) | DELA(Z) = (DELA(3) + DELA(4) + DELA(5))/3 |
| (160A) | IF Z = 10 GO TO 170 |
| (160B) | GO TO 144 |
| (170) | WOM2 = 0 N = 1 |
| (171) | FOR N = 1 TO 17 |
| (172) | T(N) = T(N) − DELA(Z) |
| (173) | HO4 = (W(N)*100)/WO*EXP SLOPE*T(N) |

| | -continued |
|---|---|
| (174) | WOM2 = WOM2 + HO4 |
| (175) | N = N + 1 |
| (176) | WOS32 = WOM2/17 |
| (177) | INT = Y(4) − T(4)*SLOPE |
| (178) | HHH4 = EXP INT*100/WO(EXP SLOPE*TAU) |
| (179) | %H$_2$O = (HHH4 + WOM32)/2 |

In summary of practice under this program part, there is an effective time-shifting of the exponential curve, with information derived from one (later) portion being introduced in another (earlier) portion and information introduced in the later portion from the modified earlier portion. There results a convergence of two functions, each defining water content percentages, at a coincident percentage. This percentage is then averaged with a percentage alternatively reached based on information derived in part from such function convergence.

Figure 7:
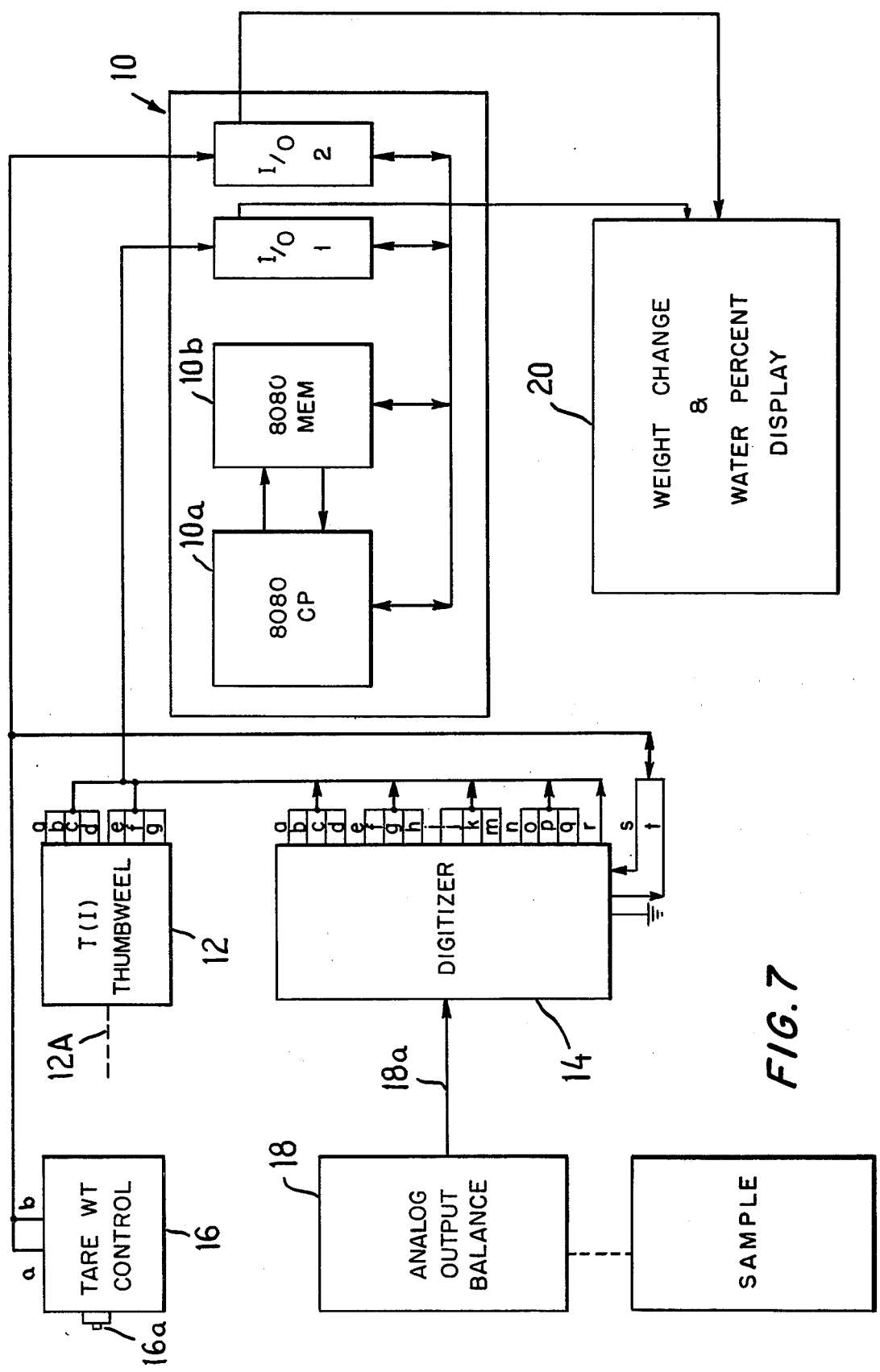
FIG. 7 is a block diagrammatic showing of apparatus for use in practicing the invention.

Referring to FIG. 7, reference numeral 10 identifies a microprocessor commercially available in kit form as Intel SDK-80 (system design kit). Component 10a is the central processor 8080 CP and 10b is the memory 8080 MEM of such kit. The kit includes an input-output unit, being shown as I/O1 (Intel 8225), and may be expanded by addition of other input-output units, one additional unit being shown as I/O2. External connections to microprocessor 10 are made to the three ports (A, B and C) of each input-output unit, each port being an eight-bit (terminal) port, as set forth in detail hereinafter.

Inputs to microprocessor 10 derive from T(I) thumbwheel 12, digitizer 14 and tare weight control 16. Input to thumbwheel 12 to establish T(I) is made by manual setting 12A. Input to tare weight control 16 is made by operation of tare push button 16A. Inputs to digitizer 14 are provided by balance 18 at line 18a and by microprocessor 10 at digitizer input line 14s.

Balance 18 may be a balance commercially available from SciTech, Boulder, Colorado as model No. SCI-TEC-222. In practice under the invention herein, such balance supports its weight pan within a microwave oven, such as is commercially available from Amana as model No. RR40W. Digitizer 14 is available commercially from Newport as panel meter model No. 2000B, and operates to provide binary-coded-decimal (BCD) outputs indicative of the analog weight measured by balance 18. Lines 14a–d, 14e–h, 14i–m and 14n–q provide four such BCD outputs in hundredths, tenths, units and tens, respectively, with line 14r indicating measurements of hundreds. Input over line 14s directs the digitizer to read the balance weight. The digitizer indicates that it has read the balance and is stabilized by output signal on line 14t, whereupon the values on lines 14a–14r are accepted by microprocessor 10.

Thumbwheel 12 furnishes BCD data on lines 12a–d indicative of units and on lines 12e–g, indicative of tens up to a tens total of seventy. Thus, the thumbwheel may be set to indicate a T(I) value up to seventy-nine seconds.

The following connections are made as between units 10, 12 and 14. Line 14a is connected to I/O1, port A, terminal 0, for brevity, noted as 1-A-O. With this shorthand notation, line 14b then to 1-A-1, 14c to 1-A-2, line 14d to 1-A-3, line 14e to 1-A-4, line 14f to 1-A-5, line 14g to 1-A-6, line 14h to 1-A-7, line 14i to 1-B-0, line 14j to 1-B-1, line 14k to 1-B-2, line 14m to 1-B-3, line 14n to 1-B-4, line 14o to 1-B-5, line 14p to 1-B-6, line 14q to 1-B-7, line 14r to 1-C-0, line 14s to 2-C-2, line 14t to 2-C-4 and lines 12a–g respectively to 1-C-1 through 1-C-7.

Tare weight control 16 is shown in FIG. 7a. On operation of tare push button TPB, line 16b provides a +5 v level to terminal 7 of port C of I/O2. Relay k1 is connected in parallel with the energizing circuitry of the microwave oven magnetron and closes its contacts k1-1. Indication of this event is provided by a line 16a +5 v level to terminal 5 of port C of I/O2.

Display 20 (FIG. 7) is supplied with information by I/O1 and I/O2 to indicate both weight change and water percent. This unit is implemented as shown in FIG. 7b by four display units 20a through 20d and inverter-driver 20e. The display units each may be comprised of a TI-008 (Texas Instruments) seven-segment decoder-driver and unit 20e may be a CD 4009 COS MOS logic chip of RCA (Radio Corporation of America).

Terminals numbered by the manufacturer as eleven, thirteen and sixteen on chips 20a–20d are connected to +5 v. Manufacturer-numbered terminals five and eight of chips 20a and 20b and five, eight and twelve of chips 20c and 20d are connected to ground. Terminals manufacturer-numbered fifteen, ten, six and seven (data-receiving) are connected to lines 20a1-4, 20b1-4, 20c1-4 and 20d1-4, respectively for chips 20a–d. Connection of these lines to microprocessor 10 is as follows: lines 20a1-4 to I/O2, port B, terminals 4 through 7; lines 20b1-4 to I/O2, port B, terminals 0 through 3; lines 20c1-4 to I/O2, port A, terminals 4 through 7; and lines 20d1-4 to I/O2, port A, terminals 0 through 3.

For chip 20e, terminals manufacturer-numbered as one and sixteen are connected to +5 v, eight to ground, four by line 20e1 to manufacturer-numbered terminal twelve (decimal display) of chip 20b and both five and six by line 20e2 to manufacturer-numbered terminal twelve of chip 20a. Chip 20e terminals three, fourteen and seven are connected in common to line 20e3 and thereby to terminal 1, port C of I/O2. Chip 20e terminal nine is connected to line 20e4 and thereby to terminal 0, port C of I/O2.

As microprocessor 10 furnishes numeric data to chips 20a–20d, it furnishes to chip 20e, by lines 20e3 and 20e4 indication of whether such data is indicative of weight change or water percent. Based on the resultant voltage levels on lines 20e1 (+5 v is data is percent) and 20e2 (+5 v is data is weight change), either unit 20a or unit 20b displays data followed by a decimal point. Lines 20e5 and 20e6 likewise alternate at +5 v in accordance with the character of the data furnished by the microprocessor to units 20a–d and, accordingly, may serve to drive such as light-emitting diode stages to visually indicate the character of displayed data.

With the foregoing system circuitry and circuit connections, the Intel 8080 may be programmed as set forth below to implement the method of the invention. Such program follows the flow chart of FIGS. 2–6 and performs the functions discussed in detail with the previously described general purpose computer program.

| | | | | | | |
|---|---|---|---|---|---|---|
| 009B | | MODEK | EQU | 9BH | ; KIT PORT A,B,C IN | |
| 0088 | | MODEU | EQU | 88H | ; USER PORT A,B,CL OUT, CU IN | |
| 00F7 | | PORT1 | EQU | 0F7H | ; KIT CONTR PORT | |
| 00EF | | PORT2 | EQU | 0EFH | ; USER CONTR PORT | |
| 00F4 | | PAK | EQU | 0F4H | ; PORT A KIT | |
| 00F5 | | PBK | EQU | 0F5H | ; PORT B KIT | |
| 00F6 | | PCK | EQU | 0F6H | ; PORT C KIT | |
| 00EC | | PAU | EQU | 0ECH | ; PORT A USER | |
| 00ED | | PBU | EQU | 0EDH | ; PORT B USER | |
| 00EE | | PCUO | EQU | 0EEH | ; PORT C USER | |
| 00EE | | PCUI | EQU | 0EEH | ; PORT C UPPER | |
| 0A3E | | STR | EQU | 0A3EH | ; MATH PKG ROUT | |
| 0D4B | | INP | EQU | 0D4BH | | |
| 0AD7 | | ADD1 | EQU | 0AD7H | | |
| 0A46 | | ZRO | EQU | 0A46H | | |
| 0A8C | | MUL | EQU | 0A8CH | | |
| 0A2F | INIT | EQU | 0A2FH | | | |
| 0AD4 | | SUB1 | EQU | 0AD4H | | |
| 0E0D | | OUT1 | EQU | 0E0DH | | |
| 0AB4 | | DIV | EQU | 0AB4H | | |
| 0A6E | | LOD | EQU | 0A6EH | | |
| 0940 | | LN | EQU | 0940H | | |
| 08A2 | | EXP | EQU | 08A2H | | |
| 0010 | | START: | ORG | 10H | | |
| 0010 | 31FD13 | | LXI | SP,13FDH | | |
| 0013 | 3E9B | | MVI | A,MODEK | ; SET I/O | |
| 0015 | D3F7 | | OUT | PORT 1 | | |
| 0017 | 3E88 | | MVI | A,MODEU | | |
| 0019 | D3EF | | OUT | PORT2 | | |
| 001B | 00 | | NOP | | | |
| 001C | 00 | | NOP | | | |
| 001D | 00 | | NOP | | | |
| 001E | 3E05 | | MVI | A,05H | ; SELECT WT, DEC, READ NOT | |
| 0020 | D3EE | | OUT | PCUO | | |
| 0022 | 00 | | NOP | | | |
| 0023 | 00 | | NOP | | | |
| 0024 | 00 | | NOP | | | |
| 0025 | 16FF | TARE: | MVI | D,0FFH | ; SET COUNT | |
| 0027 | AF | NTARE: | XRA | A | ; CLEAR CARRY | |
| 0028 | DBEE | | IN | PCUI | ; GET DATA | |
| 002A | E680 | | ANI | 80H | ; MASK TARE BIT | |
| 002C | 17 | | RAL | | | |
| 002D | D22500 | | JNC | TARE | | |
| 0030 | 15 | | DCR | D | | |
| 0031 | C22700 | | JNZ | NTARE | ; LOOP UNTIL DEBOUNCE | |
| 0034 | 16FF | DBNC: | MVI | D,0FFH | | |
| 0036 | AF | NDB: | XRA | A | | |
| 0037 | DBEE | | IN | PCUI | | |
| 0039 | E680 | | ANI | 80H | | |
| 003B | 17 | | RAL | | | |
| 003C | DA3400 | | JC | DBNC | | |
| 003F | 15 | | DCR | D | | |
| 0040 | C23600 | | JNZ | NDB | ; TARE PB RELEASED | |
| 0043 | AF | | XRA | A | ; CLEAR DISPLAY | |
| 0044 | D3EC | | OUT | PAU | | |
| 0046 | D3ED | | OUT | PBU | | |
| 0048 | CD2F0A | | CALL | INIT | | |
| 004B | 3E05 | | MVI | A,05H | | |
| 004D | D3EE | | OUT | PCUO | | |
| 004F | CD7901 | | CALL | DS | | |
| 0052 | CD0E01 | | CALL | WTA | ; GET WT AVG | |
| 0055 | 210411 | | LXI | H,TWA | | |
| 0058 | CDE0A | | CALL | STR | ; STORE TARE WT | |
| 005B | 219B12 | | LXI | H,CSB7 | | |
| 005E | 362C | | MVI | M,',' | | |
| 0060 | AF | | XRA | A | ; CLEAR CARRY | |
| 0061 | DBF6 | | IN | PCK | ; GET TS DATA | |
| 0063 | 1F | | RAR | | ; ADJUST | |
| 0064 | CD6A01 | | CALL | CONVT | ; CONVERT TO STRING | |
| 0067 | CD4B0D | | CALL | INP | ; CONVERT TO FP | |
| 006A | 215011 | | LXI | H,T1 | | |
| 006D | 22BC12 | | SHLD | SA1 | | |
| 0070 | CD3E0A | | CALL | STR | | |
| 0073 | 1E10 | | MVI | E,16 | | |
| 0075 | D5 | FT: | PUSH | D | | |
| 0076 | 2ABC12 | | LHLD | SA1 | | |
| 0079 | CD6E0A | | CALL | LOD | | |
| 007C | 21E006 | | LXI | H,CON9 | | |
| 007F | CDD70A | | CALL | ADD1 | | |
| 0082 | 2ABC12 | | LHLD | SA1 | | |
| 0085 | CDBB06 | | CALL | INRN | | |
| 0088 | 22BC12 | | SHLD | SA1 | ; SAVE NEW MEM LOC | |

| | | | -continued | | |
|---|---|---|---|---|---|
| 008B | CD3E0A | | CALL | STR | |
| 008E | 00 | | NOP | | |
| 008F | 00 | | NOP | | |
| 0090 | 00 | | NOP | | |
| 0091 | D1 | | POP | D | |
| 0092 | 1D | | DCR | E | |
| 0093 | C27500 | | JNZ | FT | ; CONTINUE T TABLE |
| 0096 | 1E44 | | MVI | E,68 | ; 4×17 |
| 0098 | 215011 | | LXI | H,T1 | |
| 009B | 019411 | | LXI | B,TI1 | |
| 009E | 7E | MB: | MOV | A,M | ; MOVE T TO TI |
| 009F | 02 | | STAX | B | |
| 00A0 | 23 | | INX | H | |
| 00A1 | 03 | | INX | B | |
| 00A2 | 1D | | DCR | E | |
| 00A3 | C29E00 | | JNZ | MB | |
| | | | | | ; |
| 00A6 | 00 | | NOP | | |
| 00A7 | 00 | | NOP | | |
| 00A8 | 00 | | NOP | | |
| 00A9 | 00 | | NOP | | |
| 00AA | DBEE | LVO: | IN | PCUI | |
| 00AC | E620 | | ANI | 20H | ; MASK FOR START |
| 00AE | FE20 | | CPI | 20H | ; OVEN ON |
| 00B0 | C2AA00 | | JNZ | LVO | |
| | | | | | ; YES |
| 00B3 | CD7901 | | CALL | D1S | |
| 00B6 | CD0E01 | | CALL | WTA | |
| 00B9 | 210011 | | LXI | H,WOT | ; STORE W + TARE |
| 00BC | CD3E0A | | CALL | STR | |
| 00BF | 210411 | | LXI | H,TWA | ; GET TARE |
| 00C2 | CDD40A | | CALL | SUB1 | ; REMOVE TARE |
| 00C5 | 210811 | | LXI | H,WO | |
| 00C8 | CD3E0A | | CALL | STR | ; STORE |
| 00CB | CDAF01 | | CALL | DTS | ; DELAY T SWITCH SETTING |
| 00CE | 210C11 | | LXI | H,W1 | |
| 00D1 | 22BE12 | | SHLD | SA2 | |
| 00D4 | 1E11 | | MVI | E,17 | |
| 00D6 | D5 | | PUSH | D | |
| 00D7 | CD0E01 | LWD: | CALL | WTA | |
| 00DA | 210011 | | LXI | H,WOT | |
| 00DD | CDD40A | | CALL | SUB1 | ; GET WT DIFFERENCE |
| 00E0 | 21C806 | | LXI | H,CON3 | |
| 00E3 | CD8C0A | | CALL | MUL | ; CORRECT SIGN |
| 00E6 | 2ABE12 | | LHLD | SA2 | |
| 00E9 | CD3E0A | | CALL | STR | |
| 00EC | CDCA01 | | CALL | OWD | ; OUTPUT WT DATA |
| 00EF | 2ABE12 | | LHLD | SA2 | |
| 00F2 | 23 | | INX | H | |
| 00F3 | 23 | | INX | H | |
| 00F4 | 23 | | INX | H | |
| 00F5 | 23 | | INX | H | |
| 00F6 | 22BE12 | | SHLD | SA2 | |
| 00F9 | D1 | | POP | D | |
| 00FA | 1D | | DCR | E | |
| 00FB | CA0501 | | JZ | COMPT | ; LOOP UNTIL WT DONE |
| 00FE | D5 | | PUSH | D | |
| 00FF | CD9101 | | CALL | D4S | ; DELAY 5 SEC |
| 0102 | C3D700 | | JMP | LWD | |
| 0105 | CD2802 | COMPT: | CALL | CMPT | |
| 0108 | CDD401 | | CALL | OMD | ; OUTPUT MOISTURE DATA |
| 010B | C32500 | | JMP | TARE | |
| | | | ; | | |
| | | | ; SUBROUTINES | | |
| | | | ; | | |
| 010E | CD460A | WTA: | CALL | ZRO | ; GETS 4 VALUES AVG |
| 0111 | 219C12 | | LXI | H,TS1 | |
| 0114 | CD3E0A | | CALL | STR | ; ZERO SUM |
| 0117 | 1E03 | | MVI | E,3 | |
| 0119 | D5 | WTA1: | PUSH | D | |
| 011A | CD2F01 | | CALL | NWT | |
| 011D | CD8501 | | CALL | D333M | |
| 0120 | D1 | | POP | D | |
| 0121 | 1D | | DCR | E | |
| 0122 | C21901 | | JNZ | WTA1 | |
| 0125 | CD2F01 | | CALL | NWT | |
| 0128 | 21C006 | | LXI | H,CON1 | |
| 012B | CD8C0A | | CALL | MUL | ; * BY .00025 FOR AVG, SCAL EG |
| 012E | C9 | | RET | | |
| | | | ; | | |
| 012F | CD3F01 | NWT: | CALL | WT | ; SUM WT ROUTINE |
| 0132 | 219C12 | | LXI | H,TS1 | |

| | | | | | |
|---|---|---|---|---|---|
| 0135 | CDD70A | | CALL | ADD1 | |
| 0138 | 219C12 | | LXI | H,TS1 | |
| 013B | CD3E0A | | CALL | STR | |
| 013E | C9 | | RET | | |

;
;

| | | | | | |
|---|---|---|---|---|---|
| 013F | 3E01 | WT: | MVI | A,01H | ; SEND HOLD TO DPM |
| 0141 | D3EE | | OUT | PCUO | |
| 0143 | DBEE | LUR: | IN | PCUI | |
| 0145 | E610 | | ANI | 10H | ; MASKH |
| 0147 | FE10 | | CPI | 10H | ; CHECK FOR READINGS |
| 0149 | C24301 | | JNZ | LUR | ; LOOP UNTIL READY |
| 014C | 219B12 | | LXI | H,CSB7 | |
| 014F | 362C | | MVI | M,',' | |
| 0151 | DBF4 | | IN | PAK | |
| 0153 | CD6A01 | | CALL | CONVT | |
| 0156 | DBF5 | | IN | PBK | |
| 0158 | CD6A01 | | CALL | CONVT | |
| 015B | DBF6 | | IN | PCK | |
| 015D | E601 | | ANI | 01H | |
| 015F | CD6A01 | | CALL | CONVT | |
| 0162 | 3E05 | | MVI | A,05H | ; RELEASE DPM |
| 0164 | D3EE | | OUT | PCUO | |
| 0166 | CD4B0D | | CALL | INP | ; CONVERT TO FP |
| 0169 | C9 | | RET | | |

;
;

| | | | | | |
|---|---|---|---|---|---|
| 016A | 2B | CONVT: | DCX | H | |
| 016B | 47 | | MOV | B,A | |
| 016C | E60F | | ANI | 0FH | |
| 016E | 77 | | MOV | M,A | |
| 016F | 2B | | DCX | H | ; UPDATE POINTER |
| 0170 | 78 | | MOV | A,B | ; GET UPPER BY TE |
| 0171 | 0F | | RRC | | ; ADJUST |
| 0172 | 0F | | RRC | | |
| 0173 | 0F | | RRC | | |
| 0174 | 0F | | RRC | | |
| 0175 | E60F | | ANI | 0FH | ; MASK |
| 0177 | 77 | | MOV | M,A | ; MOVE TO BUFFER |
| 0178 | C9 | | RET | | |
| 0179 | C5 | DIS: | PUSH | B | ; ½ SEC DELAY |
| 017A | D5 | | PUSH | D | ; |
| 017B | 1E01 | | MVI | E,01 | |
| 017D | 16FF | | MVI | D,0FFH | |
| 017F | CD9D01 | | CALL | DLY | |
| 0182 | D1 | | POP | D | |
| 0183 | C1 | | POP | B | |
| 0184 | C9 | | RET | | |

;
;

| | | | | | |
|---|---|---|---|---|---|
| 0185 | C5 | D333M: | PUSH | B | ; 333 MS DELAY |
| 0186 | D5 | | PUSH | D | |
| 0187 | 1E01 | | MVI | E,01 | |
| 0189 | 16AA | | MVI | D,0AAH | |
| 018B | CD9D01 | | CALL | DLY | |
| 018E | D1 | | POP | D | |
| 018F | C1 | | POP | B | |
| 0190 | C9 | | RET | | |

;
;

| | | | | | |
|---|---|---|---|---|---|
| :0191 | C5 | D4S: | PUSH | B | ; 4 SEC DELAY |
| 0192 | D5 | | PUSH | D | |
| 0193 | 1E08 | | MVI | E,08 | |
| 0195 | 16FF | | MVI | D,0FFH | |
| 0197 | CD9D01 | | CALL | DLY | |
| 019A | D1 | | POP | D | |
| 019B | C1 | | POP | B | |
| 019C | C9 | | RET | | |

; D=#OF FF DELAY=BASIC
; E=#OF BASIC DELAYS

| | | | | | |
|---|---|---|---|---|---|
| 019D | 1C | DLY: | INR | E | ; VARIABLE DELAY |
| 019E | 1D | NXTE: | DCR | E | |
| 019F | C8 | | RZ | | ; FINISHED |
| 01A0 | 42 | | MOV | B,D | ; WORK IN B |
| 01A1 | 04 | | INR | B | |
| 01A2 | 05 | NXTB: | DCR | B | |
| 01A3 | CA9E01 | | JZ | NXTE | |

-continued

| | | | | | |
|---|---|---|---|---|---|
| 01A6 | 0EFF | | MVI | C,0FFH | |
| 01AB | 0D | NXTC: | DCR | C | |
| 01A9 | C2A801 | | JNZ | NXTC | |
| 01AC | C3A201 | | JMP | NXTB | |
| | | ; | | | |
| | | ; | | | |
| 01AF | 215011 | DTS: | LXI | H,T1 | ; T1 IN FP |
| 01B2 | CD6E0A | | CALL | LOD | |
| 01B5 | 21C806 | NXT1: | LXI | H,CON3 | ; FP-1 |
| 01B8 | CDD70A | | CALL | ADD1 | |
| 01BB | C8 | | RZ | | ; DELAY FINISHED |
| 01BC | C5 | | PUSH | B | |
| 01BD | D5 | | PUSH | D | |
| 01BE | 1E02 | | MVI | E,02 | |
| 01C0 | 16FF | | MVI | D,0FFH | |
| 01C2 | CD9D01 | | CALL | DLY | ; DELAY 1 SEC |
| 01C5 | D1 | | POP | D | |
| 01C6 | C1 | | POP | B | |
| 01C7 | C3B501 | | JMP | NXT1 | |
| | | | | ; OUTPUT WT DATA | |
| | | | | ; FP TO CS PACKED BCD | |
| 01CA | 21DC06 | OWD: | LXI | H,CON8 | ; MPY BY 1000 |
| 01CD | CD8C0A | | CAll | MUL | |
| 01D0 | CDE201 | | CALL | ADJO | ; ADJUST OUTPUT |
| 01D3 | C9 | | RET | | |
| | | | | ; OUTPUT MOIST DATA | |
| | | | | ; VALUE IN FP ACCUM | |
| | | ; | | | |
| 01D4 | 21D006 | OMD: | LXI | H,CON5 | MPY BY 100 |
| 01D7 | CD8C0A | | CALL | MUL | |
| 01DA | CDE201 | | CALL | ADJO | |
| 01DD | 3E06 | | MVI | A,06H | |
| 01DF | D3EE | | OUT | PCUO | |
| 01E1 | C9 | | RET | | |
| 01E2 | 21A012 | ADJO: | LXI | H,TS2 | |
| 01E5 | CD0D0E | | CALL | OUT1 | |
| 01E8 | AF | | XRA | A | |
| 01E9 | D3EC | | OUT | PAU | ; CLEAR LOWER |
| 01EB | D3ED | | OUT | PBU | ; CLEAR UPPER |
| 01ED | 0E00 | | MVI | C,0 | ; CLEAR DIGIT COUNTER |
| 01EF | 21A112 | | LXI | H,TS2+1 | ; POINT TO BUFFER |
| 01F2 | 3EFE | | MVI | A,0FEH | ; SET DEC PT CHECK |
| 01F4 | BE | LZCK: | CMP | M | |
| 01F5 | CAFD01 | | JZ | OCS | |
| 01F8 | 0C | | INR | C | ; UPDATE DEC COUNT |
| 01F9 | 23 | | INX | H | ; NEST CHAR |
| 01FA | C3F401 | | JMP | LZCK | |
| 01FD | 0C | OCS: | INR | C | |
| 01FE | 0D | | DCR | C | |
| 01FF | C8 | | RZ | | ; THROUGH |
| 0200 | 2B | | DCX | H | |
| 0201 | 7E | | MOV | A,M | ; GET LSD |
| 0202 | 47 | | MOV | B,A | ; SAVE LOWER |
| 0203 | D3EC | | OUT | PAU | |
| 0205 | 0D | | DCR | C | |
| 0206 | C8 | | RZ | | ; THROUGH |
| 0207 | 2B | | DCX | H | ; GET NEXT CHAR |
| 0208 | AF | | XRA | A | ; CLEAR CARRY |
| 0209 | 7E | | MOV | A,M | |
| 020A | 07 | | RLC | | |
| 020B | 07 | | RLC | | |
| 020C | 07 | | RLC | | |
| 020D | 07 | | RLC | | |
| 020E | B0 | | ORA | B | ; COMBINE LOWER AND NEXT DIG |
| 020F | D3EC | | OUT | PAU | |
| 0211 | 0D | | DCR | C | |
| 0212 | C8 | | RZ | | |
| 0213 | 2B | | DCX | H | |
| 0214 | 7E | | MOV | A,M | |
| 0215 | 47 | | MOV | B,A | |
| 0216 | D3ED | | OUT | PBU | |
| 0218 | 0D | | DCR | C | |
| 0219 | C8 | | RZ | | |
| 021A | 2B | | DCX | H | |
| 021B | AF | | XRA | A | |
| 021C | 7E | | MOV | A,M | |
| 021D | 07 | | RLC | | |
| 021E | 07 | | RLC | | |
| 021F | 07 | | RLC | | |
| 0220 | 07 | | RLC | | |
| 0221 | B0 | | ORA | B | |
| 0222 | D3ED | | OUT | PBU | ; OUT UPPER DIGITS |

| | | | | | |
|---|---|---|---|---|---|
| 0224 | C9 | | RET | | |
| 0225 | 00 | | | NOP | |
| 0226 | 00 | | NOP | | |
| 0227 | 00 | | NOP | | |
| | | | | | ; COMPUTATION PROGRAM |
| 0228 | 1E1C | CMPT: | MVI | E,28 | ; FOR N=1 TO 7 (7*4FP) |
| 022A | 215011 | | LXI | H,T1 | ; X(N)=T(N) |
| 022E | 01D811 | | LXI | B,X1 | |
| 0230 | 7E | AGAIN: | MOV | A,M | |
| 0231 | 02 | | STAX | B | |
| 0232 | 23 | | INX | H | |
| 0233 | 03 | | INX | B | |
| 0234 | 1D | | DCR | E | |
| 0235 | C23002 | | JNZ | AGAIN | |
| | | | | | ; Y(N)=LN(WT(N+10)−WT(N)) |
| 0238 | 21F411 | | LXI | H,Y1 | |
| 023B | 22C412 | | SHLD | SA5 | ; SET Y(N) START |
| 023E | 210C11 | | LXI | H,W1 | |
| 0241 | 22C012 | | SHLD | SA3 | ; SET W(N) START |
| 0244 | 213411 | | LXI | H,W11 | |
| 0247 | 22C212 | | SHLD | SA4 | ; SET W(N+10) START |
| 024E | 1E07 | | MVI | E,7 | ; SET LOOP COUNT |
| 024C | D5 | NXTLN: | PUSH | D | |
| 024D | 2AC212 | | LHLD | SA4 | |
| 0250 | CD6E0A | | CALL | LOD | ; GET W(N+10) |
| 0253 | 2AC012 | | LHLD | SA3 | ; GET W(N) |
| 0256 | CDD40A | | CALL | SUB1 | ; SUBTRACT |
| 0259 | CD4009 | | CALL | LN | ; TAKE LOG |
| 025C | 2AC412 | | LHLD | SA5 | ; GET Y(N) |
| 025F | CD3E0A | | CALL | STR | |
| 0262 | 2AC412 | | LHLD | SA5 | ; GET NEXT I |
| 0265 | CDBB06 | | CALL | INRN | |
| 0268 | 22C412 | | SHLD | SA5 | |
| 026B | 2AC212 | | LHLD | SA4 | |
| 026E | CDBB06 | | CALL | INRN | |
| 0271 | 22C212 | | SHLD | SA4 | |
| 0274 | 2AC012 | | LHLD | SA3 | |
| 0277 | CDBB06 | | CALL | INRN | |
| 027A | 22C012 | | SHLD | SA3 | |
| 027D | D1 | | POP | D | |
| 027E | 1D | | DCR | E | |
| 027F | C24C02 | | JNZ | NXTLN | |
| 0282 | CD460A | | CALL | ZRO | ; INITIALIZE FOR |
| 0285 | 211012 | | LXI | H,SX | ; LEAST SQ FIT |
| 0288 | CD3E0A | | CALL | STR | |
| 028B | 211412 | | LXI | H,SY | |
| 028E | CD3E0A | | CALL | STR | |
| 0291 | 211812 | | LXI | H,SY2 | |
| 0294 | CD3E0A | | CALL | STR | |
| 0297 | 211C12 | | LXI | H,SX2 | |
| 029A | CD3E0A | | CALL | STR | |
| 029D | 212012 | | LXI | H,SXY | |
| 02A0 | CD3E0A | | CALL | STR | |
| 02A3 | 21D811 | | LXI | H,X1 | ; X(N) |
| 02A6 | 22C012 | | SHLD | SA3 | |
| 02A9 | 21F411 | | LXI | H,Y1 | ; Y(N) |
| 02AC | 22C212 | | SHLD | SA4 | |
| 02AF | 1E07 | | MVI | E,7 | ; FOR I=1 TO 7 |
| 02B1 | D5 | NXSQ: | PUSH | D | |
| 02B2 | 211012 | | LXI | H,SX | ; SX=SX+X(I) |
| 02B5 | CD6E0A | | CALL | LOD | |
| 02B8 | 2AC012 | | LHLD | SA3 | |
| 02BB | CDD70A | | CALL | ADD1 | |
| 02BE | 211012 | | LXI | H,SX | |
| 02C1 | CD3E0A | | CALL | STR | |
| 02C4 | 211412 | | LXI | H,SY | ; SY=SY+Y(I) |
| 02C7 | CD6E0A | | CALL | LOD | |
| 02CA | 2AC212 | | LHLD | SA4 | |
| 02CD | CDD70A | | CALL | ADD1 | |
| 02D0 | 211412 | | LXI | H,SY | |
| 02D3 | CD3E0A | | CALL | STR | |
| 02D9 | CD6E0A | | CALL | LOD | |
| 02DC | 2AC212 | | LHLD | SA4 | |
| 02DF | CD8C0A | | CALL | MUL | |
| 02E2 | 211812 | | LXI | H,SY2 | |
| 02E5 | CDD70A | | CALL | ADD1 | |
| 02E8 | 211812 | | LXI | H,SY2 | |
| 02EB | CD3E0A | | CALL | STR | |
| 02EE | 2AC012 | | LHLD | SA3 | ; SX2=SX2+X(I)**2 |
| 02F1 | CD6E0A | | CALL | LOD | |
| 02F4 | 2AC012 | | LHLD | SA3 | |
| 02F7 | CD8C0A | | CALL | MUL | |

| | | | | |
|---|---|---|---|---|
| 02FA | 211C12 | LXI | H,SX2 | |
| 02FD | CDD70A | CALL | ADD1 | |
| 0300 | 211C12 | LXI | H,SX2 | |
| 0303 | CD3E0A | CALL | STR | |
| 0306 | 2AC012 | LHLD | SA3 | ; SXY=SXY+X(I)*Y(I) |
| 0309 | CD6E0A | CALL | LOD | |
| 030C | 2AC212 | LHLD | SA4 | |
| 030F | CD8C0A | CALL | MUL | |
| 0312 | 212012 | LXI | H,SXY | |
| 0315 | CDD70A | CALL | ADD1 | |
| 0318 | 212012 | LXI | H,SXY | |
| 031B | CD3E0A | CALL | STR | |
| 031E | 2AC012 | LHLD | SA3 | ; GET NEXT I |
| 0321 | CDBB06 | CALL | INRN | |
| 0324 | 22C012 | SHLD | SA3 | |
| 0327 | 2AC212 | LHLD | SA4 | |
| 032A | CDBB06 | CALL | INRN | |
| 032D | 22C212 | SHLD | SA4 | |
| 0330 | D1 | POP | D | |
| 0331 | 1D | DCR | E | |
| 0332 | C2B102 | JNZ | NXSQ | |
| 0335 | 211012 | LXI | H,SX | ; DENOM= |
| 0338 | CD6E0A | CALL | LOD | ; XN*SX2− |
| 033B | 211012 | LXI | H,SX | ; SX**2 |
| 033E | CD8C0A | CALL | MUL | |
| 0341 | 219C12 | LXI | H,TS1 | |
| 0344 | CD3E0A | CALL | STR | |
| 0347 | 21E406 | LXI | H,XN | |
| 034A | CD6E0A | CALL | LOD | |
| 034D | 211C12 | LXI | H,SX2 | |
| 0350 | CD8C0A | CALL | MUL | |
| 0353 | 219C12 | LXI | H,TS1 | |
| 0356 | CDD40A | CALL | SUB1 | |
| 0359 | 212412 | LXI | H,DENOM | |
| 035C | CD3E0A | CALL | STR | |
| 035F | 211012 | LXI | H,SX | ; BP= |
| 0362 | CD6E0A | CALL | LOD | ; (XN*SXY−SX*SY)1 |
| 0365 | 211412 | LXI | H,SY | ; DENOM |
| 0368 | CD8C0A | CALL | MUL | |
| 036B | 219C12 | LXI | H,TS1 | |
| 036E | CD3E0A | CALL | STR | |
| 0371 | 21E406 | LXI | H,XN | |
| 0374 | CD6E0A | CALL | LOD | |
| 0377 | 212012 | LXI | H,SXY | |
| 037A | CD8C0A | CALL | MUL | |
| 037D | 219C12 | LXI | H,TS1 | |
| 0380 | CDD40A | CALL | SUB1 | |
| 0383 | 212412 | LXI | H,DENOM | |
| 0386 | CDB40A | CALL | DIV | |
| 0389 | 212812 | LXI | H,BP | |
| 038C | CD3E0A | CALL | STR | |
| 038F | 212812 | LXI | H,BP | ; (SY−BP*SX)1XN |
| 0392 | CD6E0A | CALL | LOD | |
| 0395 | 211012 | LXI | H,SX | |
| 0398 | CD8C0A | CALL | MUL | |
| 039B | 219C12 | LXI | H,TS1 | |
| 039E | CD3E0A | CALL | STR | |
| 03A1 | 211412 | LXI | H,SY | |
| 03A4 | CD6E0A | CALL | LOD | |
| 03A7 | 219C12 | LXI | H,TS1 | |
| 03AA | CDD40A | CALL | SUB1 | |
| 03AD | 21E406 | LXI | H,XN | |
| 03B0 | CDB40A | CALL | DIV | |
| 03B3 | 212C12 | LXI | H,AP | |
| 03B6 | CD3E0A | CALL | STR | |
| 03B9 | 215C11 | LXI | H,T4 | |
| 03BC | CD6E0A | CALL | LOD | |
| 03BF | 212812 | LXI | H,BP | |
| 032C | CD8C0A | CALL | MUL | |
| 03C5 | 212C12 | LXI | H,AP | |
| 03C8 | CDD70A | CALL | ADD1 | |
| 03CB | 210012 | LXI | H,Y4 | |
| 03CE | CD3E0A | CALL | STR | |
| 03D1 | CD460A | CALL | ZRO | |
| 03D4 | 213812 | LXI | H,DELA0 | |
| 03D7 | 22C012 | SHLD | SA3 | ; SET SA3 FOR K |
| 03DA | CD3E0A | CALL | STR | ; SET DELA0=0 |
| 03DD | AF | XRA | A | |
| 03DE | 32CC12 | STA | K | ; CLEAR K NOT EQUL TO 0 FLAG |
| 03E1 | CD460A NXT73: | CALL | ZRO | ; HOMO=0 |
| 03E4 | 213012 | LXI | H,HOMO | |
| 03E7 | CD3E0A | CALL | STR | |

| | | | | | |
|---|---|---|---|---|---|
| 03EA | 21C411 | | LXI | H,TI13 | |
| 03ED | 22C212 | | SHLD | SA4 | |
| 03F0 | 218011 | | LXI | H,T13 | |
| 03F3 | 22C412 | | SHLD | SA5 | |
| 03F6 | 213C11 | | LXI | H,W13 | |
| 03F9 | 22C612 | | SHLD | SA6 | |
| 03FC | 1E03 | | MVI | E,3 | ; SET 13 TO 15 COUNT |
| 03FE | D5 | NV: | PUSH | D | |
| 03FF | 2AC212 | | LHLD | SA4 | ; T(N)=TI(N)−DELAC(K) |
| 0402 | CD6E0A | | CALL | LOD | |
| 0405 | 2AC012 | | LHLD | SA3 | |
| 0408 | CDD40A | | CALL | SUB1 | |
| 040B | 2AC412 | | LHLD | SA5 | |
| 040E | CD3E0A | | CALL | STR | |
| | | | | | ; HON=1−EXP(BP*T(N)) |
| 0411 | 212812 | | LXI | H,BP | |
| 0414 | CD8C0A | | CALL | MUL | |
| 0417 | CDA208 | | CALL | EXP | |
| 041A | 219C12 | | LXI | H,TS1 | |
| 041D | CD3E0A | | CALL | STR | |
| 0420 | 21CC06 | | LXI | H,CON4 | |
| 0423 | CD6E0A | | CALL | LOD | |
| 0426 | 219C12 | | LXI | H,TS1 | |
| 0429 | CDD40A | | CALL | SUB1 | |
| 042C | 210811 | | LXI | H,WO | ; HOM=WT(N)1(WO*HON)*100 |
| 042F | CD8C0A | | CALL | MUL | |
| 0432 | 219C12 | | LXI | H,TS1 | |
| 0435 | CD3E0A | | CALL | STR | |
| 0438 | 2AC612 | | LHLD | SA6 | |
| 043B | CD6E0A | | CALL | LOD | |
| 043E | 219C12 | | LXI | H,TS1 | |
| 0441 | CDB40A | | CALL | DIV | |
| 0444 | 21D006 | | LXI | H,CON5 | |
| 0447 | CD8C0A | | CALL | MUL | |
| 044A | 213012 | | LXI | H,HOMO | ; HOMO=HOMO+HOM |
| 044D | CDD70A | | CALL | ADD1 | |
| 0450 | 213012 | | LXI | H,HOMO | |
| 0453 | CD3E0A | | CALL | STR | |
| 0456 | 2AC212 | | LHLD | SA4 | ; UPDATE |
| 0459 | CDBB06 | | CALL | INRN | |
| 045C | 22C212 | | SHLD | SA4 | ; TI(N) |
| 045F | 2AC412 | | LHLD | SA5 | |
| 0462 | CDBB06 | | CALL | INRN | |
| 0465 | 22C412 | | SHLD | SA5 | ; T(N) |
| 0468 | 2AC612 | | LHLD | SA6 | |
| 046B | CDBB06 | | CALL | INRN | |
| 046E | 22C612 | | SHLD | SA6 | ; WT(N) |
| 0471 | D1 | | POP | D | |
| 0472 | 1D | | DCR | E | |
| 0473 | C2FE03 | | JNZ | NV | |
| 0476 | 213012 | | LXI | H,HOMO | ; HOMO= |
| 0479 | CD6E0A | | CALL | LOD | |
| 047C | 21C406 | | LXI | H,CON2 | ; HOMO/3 |
| 047F | CDB40A | | CALL | DIV | |
| 0482 | 213012 | | LXI | H,HOMO | |
| 0485 | CD3E0A | | CALL | STR | |
| 0488 | 214412 | | LXI | H,DELA3 | |
| 048B | 22CA12 | | SHLD | SA8 | |
| 048E | 216812 | | LXI | H,TM3 | ; N=3 TO 5 |
| 0491 | 22C212 | | SHLD | SA4 | |
| 0494 | 211411 | | LXI | H,W3 | |
| 0497 | 22C412 | | SHLD | SA5 | |
| 049A | 219C11 | | LXI | H,TI3 | |
| 049D | 22C612 | | SHLD | SA6 | |
| 04A0 | 1E03 | | MVI | E,3 | |
| 04A2 | D5 | NXTV2: | PUSH | D | |
| 04A3 | 21CC06 | | LXI | H,CON4 | |
| 04A6 | CD6E0A | | CALL | LOD | |
| 04A9 | 212812 | | LXI | H,BP | |
| 04AC | CDB40A | | CALL | DIV | |
| 04AF | 219C12 | | LXI | H,TS1 | |
| 04B2 | CD3E0A | | CALL | STR | |
| 04B5 | 213012 | | LXI | H,HOMO | |
| 04B8 | CD6E0A | | CALL | LOD | |
| 04BB | 210811 | | LXI | H,WO | |
| 04BE | CD8C0A | | CALL | MUL | |
| 04C1 | 21A012 | | LXI | H,TS2 | |
| 04C4 | CD3E0A | | CALL | STR | |
| 04C7 | 2AC412 | | LHLD | SA5 | |
| 04CA | CD6E0A | | CALL | LOD | |
| 04CD | 21D006 | | LXI | H,CON5 | |
| 04D0 | CD8C0A | | CALL | MUL | |

-continued

| | | | | |
|---|---|---|---|---|
| 04D3 | 21A012 | | LXI | H,TS2 |
| 04D6 | CDB40A | | CALL | DIV |
| 04D9 | 21A012 | | LXI | H,TS2 |
| 04DC | CD3E0A | | CALL | STR |
| 04DF | 21CC06 | | LXI | H,CON4 |
| 04E2 | CD6E0A | | CALL | LOD |
| 04E5 | 00 | | NOP | |
| 04E6 | 00 | | NOP | |
| 04E7 | 00 | | NOP | |
| 04E8 | 00 | | NOP | |
| 04E9 | 00 | | NOP | |
| 04EA | 00 | | NOP | |
| 04EB | 00 | | NOP | |
| 04EC | 00 | | NOP | |
| 04ED | 21A012 | | LXI | H,TS2 |
| 04F0 | CDD40A | | CALL | SUB1 |
| 04F3 | CD4009 | | CALL | LN |
| 04F6 | 219C12 | | LXI | H,TS1 |
| 04F9 | CD8C0A | | CALL | MUL |
| 04FC | 2AC212 | | LHLD | SA4 |
| 04FF | CD3E0A | | CALL | STR |
| 0502 | 2AC612 | | LHLD | SA6                ; DELA(N)=TI(N)−TM(N) |
| 0505 | CD6E0A | | CALL | LOD |
| 0508 | 2AC212 | | LHLD | SA4 |
| 050B | CDD40A | | CALL | SUB1 |
| 050E | 2ACA12 | | LHLD | SA8 |
| 0511 | CD3E0A | | CALL | STR |
| 0514 | 2ACA12 | | LHLD | SA8                ; UPDATE SUBSCRIPT |
| 0517 | CDBB06 | | CALL | INRN |
| 051A | 22CA12 | | SHLD | SA8 |
| 051D | 2AC212 | | LHLD | SA4 |
| 0520 | CDBB06 | | CALL | INRN |
| 0523 | 22C212 | | SHLD | SA4 |
| 0526 | 2AC412 | | LHLD | SA5 |
| 0529 | CDBB06 | | CALL | INRN |
| 052C | 22C412 | | SHLD | SA5 |
| 052F | 2AC612 | | LHLD | SA6 |
| 0532 | CDBB06 | | CALL | INRN |
| 0535 | 22C612 | | SHLD | SA6 |
| 0538 | D1 | | POP | D |
| 0539 | 1D | | DCR | E |
| 053A | C2A204 | | JNZ | NXTV2 |
| 053D | 3ACC12 | | LDA | K                    ; I FK=0 K=5 |
| 0540 | FE00 | | CPI | 00H               ; CHECK FOR K=0 |
| 0542 | C25005 | | JNZ | NXTK            ; JUMP IT K NOT EQUL TO 0 |
| 0545 | 3E05 | | MVI | A,5 |
| 0547 | 32CC12 | | STA | K                    ; SET K=5 |
| 054A | 214C12 | | LXI | H,DELA5 |
| 054D | 22C012 | | SHLD | SA3               ; MODIFY K |
| 0550 | 21CC12 | NXTK: | LXI | H,K |
| 0553 | 34 | | INR | M |
| 0554 | 2AC012 | | LHLD | SA3 |
| 0557 | CDBB06 | | CALL | INRN           ; UPDATE K |
| 055A | 22C012 | | SHLD | SA3 |
| 055D | 214412 | | LXI | H,DELA3       ; DELA(K)=DELA3+DELA4+DELA5 |
| 0560 | CD6E0A | | CALL | LOD |
| 0563 | 214812 | | LXI | H,DELA4 |
| 0566 | CDD70A | | CALL | ADD1 |
| 0569 | 214C12 | | LXI | H,DELA5 |
| 056C | CDD70A | | CALL | ADD1 |
| 056F | 21C406 | | LXI | H,CON2 |
| 0572 | CDB40A | | CALL | DIV |
| 0575 | 2AC012 | | LHLD | SA3               ; GET DELAK |
| 0578 | CD3E0A | | CALL | STR                ; STORE |
| 057B | CACC12 | | LDA | K |
| 057E | FE0A | | CPI | 10 |
| 0580 | C2E103 | | JNZ | NXT73         ; JMP IF K NOT EQUL TO 10 |
| 0583 | CD460A | | CALL | ZRO |
| 0586 | 218012 | | LXI | H,WOM2 |
| 0589 | CD3E0A | | CALL | STR                 ; WOM2=0 |
| 058C | 219411 | | LXI | H,TI1               ; SET TI(N) |
| 058F | 22C212 | | SHLD | SA4 |
| 0592 | 215011 | | LXI | H,T1                ; SET T(N) |
| 0595 | 22C412 | | SHLD | SA5 |
| 0598 | 210C11 | | LXI | H,W1              ; SET W(N) |
| 059B | 22C612 | | SHLD | SA6 |
| 059E | 1E11 | | MVI | E,17                ; SET LOOP COUNT |
| 05A0 | D5 | NXTV3: | PUSH | D |
| 05A1 | 2AC212 | | LHLD | SA4 |
| 05A4 | CD6E0A | | CALL | LOD |
| 0547 | 216012 | | LXI | H,DEL10 |
| 05AA | CDD40A | | CALL | SUB1 |

| | | | | |
|---|---|---|---|---|
| 05AD | 2AC412 | LHLD | SA5 | |
| 05B0 | CD3E0A | CALL | STR | |
| 05B3 | 212812 | LXI | H,BP | |
| 05B6 | CD6E0A | CALL | LOD | |
| 05B9 | 2AC412 | LHLD | SA5 | |
| 05BC | CD8C0A | CALL | MUL | |
| 05BF | CDA208 | CALL | EXP | |
| 05C2 | 219C12 | LXI | H,TS1 | |
| 05C5 | CD3E0A | CALL | STR | |
| 05C8 | 21CC06 | LXI | H,CON4 | |
| 05CB | CD6E0A | CALL | LOD | |
| 05CE | 219C12 | LXI | H,TS1 | |
| 05D1 | CDD40A | CALL | SUB1 | |
| 05D4 | 217412 | LXI | H,WOS4 | |
| 05D7 | CD3E0A | CALL | STR | |
| 05DA | 210811 | LXI | H,WO | |
| 05DD | CD8C0A | CALL | MUL | |
| 05E0 | 219C12 | LXI | H,TS1 | |
| 05E3 | CD3E0A | CALL | STR | |
| 05E6 | 2AC612 | LHLD | SA6 | |
| 05E9 | CD6E0A | CALL | LOD | |
| 05EC | 219C12 | LXI | H,TS1 | |
| 05EF | CDB40A | CALL | DIV | |
| 05F2 | 21D006 | LXI | H,CON5 | |
| 05F5 | CD8C0A | CALL | MUL | |
| 05F8 | 217812 | LXI | H,HO4 | |
| 05FB | CD3E0A | CALL | STR | |
| 05FE | 218012 | LXI | H,WOM2 | |
| 0601 | CDD70A | CALL | ADD1 | |
| 0604 | 218012 | LXI | H,WOM2 | |
| 0607 | CD3E0A | CALL | STR | |
| 060A | 2AC212 | LHLD | SA4 | ; UPDATE TI(N) |
| 060D | CDBB06 | CALL | INRN | |
| 0610 | 22C212 | SHLD | SA4 | |
| 0613 | 2AC412 | LHLD | SA5 | ; UPDATE T(N) |
| 0616 | CDBB06 | CALL | INRN | |
| 0619 | 22C412 | SHLD | SA5 | |
| 061C | 2AC612 | LHLD | SA6 | ; UPDATE W(N) |
| 061F | CDBB06 | CALL | INRN | |
| 0622 | 22C612 | SHLD | SA6 | |
| 0625 | D1 | POP | D | |
| 0626 | 1D | DCR | E | |
| 0627 | C2A005 | JNZ | NXTV3 | |
| 062A | 218012 | LXI | H,WOM2 | ; WOS32=WOM2/17 |
| 062D | CD6E0A | CALL | LOD | |
| 0630 | 21D406 | LXI | H,CON6 | |
| 0633 | CDB40A | CALL | DIV | |
| 0636 | 218412 | LXI | H,WOS32 | |
| 0639 | CD3E0A | CALL | STR | |
| 063C | 215C11 | LXI | H,T4 | |
| 063F | CD6E0A | CALL | LOD | |
| 0642 | 212812 | LXI | H,BP | |
| 0645 | CD8C0A | CALL | MUL | |
| 0648 | 219C12 | LXI | H,TS1 | |
| 064B | CD3E0A | CALL | STR | |
| 064E | 210012 | LXI | H,Y4 | |
| 0651 | CD6E0A | CALL | LOD | |
| 0654 | 219C12 | LXI | H,TS1 | |
| 0657 | CDD40A | CALL | SUB1 | |
| 065A | 212C12 | LXI | H,AP | |
| 065D | CD3E0A | CALL | STR | |
| 0660 | 212812 | LXI | H,BP | |
| 0663 | CD6E0A | CALL | LOD | |
| 0666 | 21E806 | LXI | H,TAU | |
| 0669 | CD8C0A | CALL | MUL | |
| 066C | CDA208 | CALL | EXP | |
| 066F | 219C12 | LXI | H,TS1 | |
| 0672 | CD3E0A | CALL | STR | |
| 0675 | 21CC06 | LXI | H,CON4 | |
| 0678 | CD6E0A | CALL | LOD | |
| 067B | 219C12 | LXI | H,TS1 | |
| 067E | CDD40A | CALL | SUB1 | |
| 0681 | 219C12 | LXI | H,TS1 | |
| 0684 | CD3E0A | CALL | STR | |
| 0687 | 212C12 | LXI | H,AP | |
| 068A | CD6E0A | CALL | LOD | |
| 068D | CDA208 | CALL | EXP | |
| 0690 | 219C12 | LXI | H,TS1 | |
| 0693 | CDB40A | CALL | DIV | |
| 0696 | 218C12 | LXI | H,HHH4 | |
| 0699 | CD3E0A | CALL | STR | |
| 069C | 210811 | LXI | H,WO | |

-continued

| | | | | | |
|---|---|---|---|---|---|
| 069F | CDB40A | | CALL | DIV | |
| 06A2 | 21D006 | | LXI | H,CON5 | |
| 06A5 | CD8C0A | | CALL | MUL | |
| 06A8 | 217C12 | | LXI | H,HH04 | |
| 06AB | CD3E0A | | CALL | STR | |
| 06AE | 218412 | | LXI | H,WOS32 | |
| 06B1 | CDD70A | | CALL | ADD1 | |
| 06B4 | 21D806 | | LXI | H,CON7 | |
| 06B7 | CD8C0A | | CALL | MUL | |
| 06BA | C9 | | RET | | |
| 06BB | 23 | INRN: | INX | H | |
| 06BC | 23 | | INX | H | |
| 06BD | 23 | | INX | H | |
| 06BE | 23 | | INX | H | |
| 06BF | C9 | | RET | | |
| 06C0 | 75 | CON1: | DB | 75H | ; FP .00025 |
| 06C1 | 03 | | DB | 03H | |
| 06C2 | 12 | | DB | 12H | |
| 06C3 | 6E | | DB | 6EH | |
| 06C4 | 82 | CON2: | DB | 82H | ; FP 3.0 |
| 06C5 | 40 | | DB | 40H | |
| 06C6 | 00 | | DB | 00H | |
| 06C7 | 00 | | DB | 00H | |
| 06C8 | 81 | CON3: | DB | 81H | ; FP −1.0 |
| 06C9 | 80 | | DB | 80H | |
| 06CA | 00 | | DB | 00H | |
| 06CB | 00 | | DB | 00H | |
| 06CC | 81 | CON4: | DB | 81H | ; FP 1.0 |
| 06CD | 00 | | DB | 00H | |
| 06CE | 00 | | DB | 00H | |
| 06CF | 00 | | DB | 00H | |
| 06D0 | 87 | CON5: | DB | 87H | ; FP 100 |
| 06D1 | 48 | | DB | 48H | |
| 06D2 | 00 | | DB | 00H | |
| 06D3 | 00 | | DB | 00H | |
| 06D4 | 85 | CON6: | DB | 85H | ; FP 17 |
| 06D5 | 08 | | DB | 08H | |
| 06D6 | 00 | | DB | 00H | |
| 06D7 | 00 | | DB | 00H | |
| 06D8 | 80 | CON7: | DB | 80H | ; FP .5 |
| 06D9 | 00 | | DB | 00H | |
| 06DA | 00 | | DB | 00H | |
| 06DB | 00 | | DB | 00H | |
| 06DC | 8A | CON8: | DB | 8AH | ; FP 1000 |
| 06DD | 7A | | DB | 7AH | |
| 06DE | 00 | | DB | 00H | |
| 06DF | 00 | | DB | 00H | |
| 06E0 | 83 | CON9: | DB | 83H | ; FP 5.0 |
| 06E1 | 20 | | DB | 20H | |
| 06E2 | 00 | | DB | 00H | |
| 06E3 | 00 | | DB | 00H | |
| 06E4 | 83 | XN: | DB | 83H | ; FP 7.0 |
| 06E5 | 60 | | DB | 60H | |
| 06E6 | 00 | | DB | 00H | |
| 06E7 | 00 | | DB | 00H | |
| 06E8 | 86 | TAU: | DB | 86H | ; FP 50.0 |
| 06E9 | 48 | | DB | 48H | |
| 06EA | 00 | | DB | 00H | |
| 06EB | 00 | | DB | 00H | |
| 1000 | | | ORG | 1000H | |
| 1000 | | | DS | 256 | ; MATH SCRATCH PAD |
| 1100 | | | ORG | 1100H | |
| 1100 | | WOT: | DS | 4 | ; WT WITH TARE |
| 1104 | | TWA: | DS | 4 | ; TARE WT AVG |
| 1108 | | WO: | DS | 4 | ; INITIAL WT |
| 110C | | W1: | DS | 4 | ; |
| 1110 | | W2: | DS | 4 | |
| 1114 | | W3: | DS | 4 | |
| 1118 | | W4: | DS | 4 | |
| 111C | | W5: | DS | 4 | |
| 1120 | | W6: | DS | 4 | |
| 1124 | | W7: | DS | 4 | |
| 1128 | | W8: | DS | 4 | |
| 112C | | W9: | DS | 4 | |
| 1130 | | W10: | DS | 4 | |
| 1134 | | W11: | DS | 4 | |
| 1138 | | W12: | DS | 4 | |
| 113C | | W13: | DS | 4 | |
| 1140 | | W14: | DS | 4 | |
| 1144 | | W15: | DS | 4 | |
| 1148 | | W16: | DS | 4 | |
| 114C | | W17: | DS | 4 | |

-continued

| | | | |
|---|---|---|---|
| 1150 | T1: | DS | 4 |
| 1154 | T2: | DS | 4 |
| 1158 | T3: | DS | 4 |
| 115C | T4: | DS | 4 |
| 1160 | T5: | DS | 4 |
| 1164 | T6: | DS | 4 |
| 1168 | T7: | DS | 4 |
| 116C | T8: | DS | 4 |
| 1170 | T9: | DS | 4 |
| 1174 | T10: | DS | 4 |
| 1178 | T11: | DS | 4 |
| 117C | T12: | DS | 4 |
| 1180 | T13: | DS | 4 |
| 1184 | T14: | DS | 4 |
| 1188 | T15: | DS | 4 |
| 118C | T16: | DS | 4 |
| 1190 | T17: | DS | 4 |
| 1194 | TI1: | DS | 4 |
| 1198 | TI2: | DS | 4 |
| 119C | TI3: | DS | 4 |
| 11A0 | TI4: | DS | 4 |
| 11A4 | TI5: | DS | 4 |
| 11A8 | TI6: | DS | 4 |
| 11AC | TI7: | DS | 4 |
| 11B0 | TI8: | DS | 4 |
| 11B4 | TI9: | DS | 4 |
| 11B8 | TI10: | DS | 4 |
| 11BC | TI11: | DS | 4 |
| 11C0 | TI12: | DS | 4 |
| 11C4 | TI13: | DS | 4 |
| 11C8 | TI14: | DS | 4 |
| 11CC | TI15: | DS | 4 |
| 11D0 | TI16: | DS | 4 |
| 11D4 | TI17: | DS | 4 |
| 11D8 | X1: | DS | 4 |
| 11DC | X2: | DS | 4 |
| 11E0 | X3: | DS | 4 |
| 11E4 | X4: | DS | 4 |
| 11E8 | X5: | DS | 4 |
| 11EC | X6: | DS | 4 |
| 11F0 | X7: | DS | 4 |
| 11F4 | Y1: | DS | 4 |
| 11F8 | Y2: | DS | 4 |
| 11FC | Y3: | DS | 4 |
| 1200 | Y4: | DS | 4 |
| 1204 | Y5: | DS | 4 |
| 1208 | Y6: | DS | 4 |
| 120C | Y7: | DS | 4 |
| 1210 | SX: | DS | 4 |
| 1214 | SY: | DS | 4 |
| 1218 | SY2: | DS | 4 |
| 121C | SX2: | DS | 4 |
| 1220 | SXY: | DS | 4 |
| 1224 | DENOM: | DS | 4 |
| 1228 | BP: | DS | 4 |
| 122C | AP: | DS | 4 |
| 1230 | HOMO: | DS | 4 |
| 1234 | HOM: | DS | 4 |
| 1238 | DELA0: | DS | 4 |
| 123C | DELA1: | DS | 4 |
| 1240 | DELA2: | DS | 4 |
| 1244 | DELA3: | DS | 4 |
| 1248 | DELA4: | DS | 4 |
| 124C | DELA5: | DS | 4 |
| 1250 | DELA6: | DS | 4 |
| 1254 | DELA7: | DS | 4 |
| 1258 | DELA8: | DS | 4 |
| 125C | DELA9: | DS | 4 |
| 1260 | DEL10: | DS | 4 |
| 1264 | DEL11: | DS | 4 |
| 1268 | TM3: | DS | 4 |
| 126C | TM4: | DS | 4 |
| 1270 | TM5: | DS | 4 |
| 1274 | WOS4: | DS | 4 |
| 1278 | HO4: | DS | 4 |
| 127C | HH04: | DS | 4 |
| 1280 | WOM2: | DS | 4 |
| 1284 | WOS32: | DS | 4 |
| 1288 | INC: | DS | 4 |
| 128C | HHH4: | DS | 4 |
| 1290 | MEAN: | DS | 4 |

;

| | | | | | |
|---|---|---|---|---|---|
| 1294 | CSB0: | DS | 1 | ; 7 DIG CS BUF | |
| 1295 | CSB1: | DS | 1 | | |
| 1296 | CSB2: | DS | 1 | | |
| 1297 | CSB3: | DS | 1 | | |
| 1298 | CSB4: | DS | 1 | | |
| 1299 | CSB5: | DS | 1 | ; LSD+1 | |
| 129A | CSB6: | DS | 1 | ; LSD | |
| 129B | CSB7: | DS | 1 | ; , | |
| 129C | TS1: | DS | 4 | | |
| 12A0 | TS2: | DS | 4 | | |
| 12A4 | TS3: | DS | 4 | | |
| 12A8 | TS4: | DS | 4 | | |
| 12AC | TS5: | DS | 4 | | |
| 12B0 | TS6: | DS | 4 | | |
| 12B4 | TS7: | DS | 4 | | |
| 12B8 | TS8: | DS | 4 | | |
| 12BC | SA1: | DS | 2 | ; T ADDRESS | |
| 12BE | SA2: | DS | 2 | ; W ADDRESS | |
| 12C0 | SA3: | DS | 2 | | |
| 12C2 | SA4: | DS | 2 | | |
| 12C4 | SA5: | DS | 2 | | |
| 12C6 | SA6: | DS | 2 | | |
| 12C8 | SA7: | DS | 2 | | |
| 12CA | SA8: | DS | 2 | | |
| 12CC | K: | DS | 1 | | |
| 0000 | | END | | | |

While the oven in which the balance is placed in the foregoing discussion is identified as a microwave oven, sample heating may otherwise be accommodated by such as radiative, convective and electrical resistance heating. Microwave heating is preferred for water volatilization, however, since water has known higher absorptivity to microwave heating that do most other volatiles. While the volatile of interest in the foregoing discussion is identified as water, particularly with the volatilecontainment material as tobacco, the invention will be seen as having applicability to volatilizable substances other than water in matter other than tobacco.

The parameter T(I) is a variable, presettable in accordance with the volatile content character of the sample and the intensity of the heating energy. In respect of tobacco, for example, certain species have particularly high water content and T(I) may be selected to be a time substantially less than the time for T(I) which would be selected for species of lower water content. In this connection, applicant has found that some time need elapse prior to taking weight measurements for use in volatile percent determination in order to obtain measurements as to which the noted exponential relation applies. Further, the parameters IV and TAU, selected above at five and fifty seconds, respectively, are otherwise preselectable. Thus, IV may define other constant time intervals between the taking of weight measurements and TAU is any integral multiple of the selected IV time extent. In the foregoing, TAU is selected as a multiple of ten of IV. By the phrase integral multiple is meant twice or greater, whereby the weight differencing of successively taken weights is precluded.

In comparative evaluation of practice under the invention and the customary O.V. practice discussed above, a sample tobacco blend was separated into two parts. One part was placed in a forced draft laboratory oven and heated for three hours at 100° C. The other part was processed in accordance with the invention. In both cases, the volatiles given off during heating were collected and analyzed both qualitatively and quantitatively. Water was the only volatile found in the practice according with the invention. In the other practice, i.e., forced draft over heating, volatiles other than water were found in weight amount approximately one-thirteenth by weight of the weight amount of volatilized water. In summary of the foregoing and by way of introduction to the claims, there has been disclosed a method for use in determining volatile content of a sample. Weight values are taken at a first time, $t_1$ (FIG. 1) which is spaced from the start of a heating course by a first predetermined measure of time, T(I). Weight values are then taken at a plurality of times ($t_2$-$t_{17}$), times $t_1$ through $t_{17}$ being uniformly spaced by a second predetermined measure shown as IV in FIG. 1. Differences are then obtained between weight values taken at times separated from one another by a measure of time (TAU, FIG. 1), which is an integral multiple of the second predetermined measure of time. Such taking of weight values and subtraction of weight values is controlled and scheduled by a computer. From such data collection and grouping, one may proceed to further computer controlled and scheduled practices for identifying the volatile content of a sample.

Various changes and modifications may be introduced in the foregoing particularly described methods without departing from the invention. Such methods are thus intended in a descriptive and not in a limiting sense. The true spirit and scope of the invention is set forth in the following claims.

What is claimed is:

1. A method for use in determining volatile content of a sample comprising the steps of:
    (a) weighing said sample to obtain the weight thereof; then
    (b) heating said sample; and
    (c) during the course of such heating of said sample, weighing said sample
        (1) at a first time spaced from the start of such heating course by a first predetermined measure of time, and
        (2) at a plurality of subsequent times, said subsequent times beginning with an initial time spaced by a second predetermined measure of time from said first time and each being uniformly spaced one from the other by said second predetermined measure of time; and
    (d) obtaining differences between said weights obtained in said step (c) which are taken at times separated from one another by a measure of time which is an integral multiple of said second predetermined measure, said steps (c) and (d) being controlled and scheduled by a computer.

2. The method claimed in claim 1 including the further step, controlled and scheduled by a computer, of determining natural logarithms of such weight differences and identifying characteristics of a linear relationship between such natural logarithms and selected of said step (c) times.

3. The method claimed in claim 2 wherein said identifying of said linear relationship is controlled and scheduled by a computer and obtained by determining least squares fit of said natural logarithms and said selected step (c) times.

4. The method claimed in claim 3 including the further steps, controlled and scheduled by a computer, of determining slope and intercept values defining said linear relationship.

5. The method claimed in claim 4 wherein said volatile content is determined, under control and scheduling by a computer, as a function of said weight differences, said weight obtained in said step (a) and such determined slope.

6. The method claimed in claim 4 wherein said volatile content is determined, under control and scheduling by a computer, as a function of said weight obtained in said step (a), such determined slope, such determined intercept and said integral multiple of said second predetermined measure.

7. The method claimed in claim 4 wherein said volatile content is determined, under control and scheduling by a computer, as a function of said weight differences, said weight obtained in said step (a) and such determined slope and further as a function of said weight obtained in said step (a), such determined slope, such determined intercept and said integral multiple of said second predetermined measure.

8. The method claimed in claim 1 wherein said sample is tobacco and said volatile content is water.

* * * * *

Notice of Adverse Decision in Interference

In Interference No. 100,734, involving Patent No. 4,168,623, C. E. Thomas, Jr., METHOD FOR DETERMINING VOLATILE CONTENT OF A SAMPLE, final judgment adverse to the patentee was rendered June 25, 1982, as to claims 1–8.

[*Official Gazette October 19, 1982.*]